(12) United States Patent
Navia et al.

(10) Patent No.: US 11,241,313 B2
(45) Date of Patent: Feb. 8, 2022

(54) APPARATUSES AND METHODS FOR AT LEAST PARTIALLY SUPPORTING A VALVE LEAFLET OF A REGURGITANT HEART VALVE

(71) Applicant: THE CLEVELAND CLINIC FOUNDATION, Cleveland, OH (US)

(72) Inventors: Jose L. Navia, Shaker Hts., OH (US); Samir Kapadia, Chagrin Falls, OH (US); Marwane Berrada, Beachwood, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 223 days.

(21) Appl. No.: 16/712,059

(22) Filed: Dec. 12, 2019

(65) Prior Publication Data
US 2020/0113687 A1    Apr. 16, 2020

Related U.S. Application Data

(62) Division of application No. 15/677,470, filed on Aug. 15, 2017, now Pat. No. 10,537,432.
(Continued)

(51) Int. Cl.
*A61F 2/24* (2006.01)
(52) U.S. Cl.
CPC .......... *A61F 2/2442* (2013.01); *A61F 2/2454* (2013.01); *A61F 2/2466* (2013.01);
(Continued)
(58) Field of Classification Search
CPC ........ A61F 2/24; A61F 2/2412; A61F 2/2442; A61F 2/52466; A61F 2/2418
(Continued)

(56) References Cited

U.S. PATENT DOCUMENTS 5,725,552 A    3/1998   Kotula et al.
5,846,261 A    12/1998  Kotula et al.
(Continued)

FOREIGN PATENT DOCUMENTS

EP    2591755 A1    5/2013
WO    2006/041877 A2   4/2006
(Continued)

OTHER PUBLICATIONS

PCT International Search Report and Written Opinion for corresponding International Application Serial No. PCT/US2017/046912, dated Oct. 11, 2017, pp. 1-13.

*Primary Examiner* — Suzette J Gherbi
(74) *Attorney, Agent, or Firm* — Tarolli, Sundheim, Covell & Tummino LLP

(57) ABSTRACT

An apparatus for partially supporting a leaflet of a regurgitant heart valve comprises at least one subvalvular device including a subvalvular supporting portion including a leaflet-contacting upper supporter surface longitudinally spaced from an oppositely facing lower supporter surface. A supporter perimeter wall extends longitudinally between the upper and lower supporter surfaces, with at least a portion contacting a subvalvular cardiac wall adjacent to the heart valve. An anchor portion is adjacent to, and longitudinally spaced from, the upper supporter surface. The anchor portion includes a leaflet-contacting lower anchor surface longitudinally spaced from an oppositely facing upper anchor surface. A connector neck is interposed longitudinally between, and is directly attached to both of, the upper supporter surface and the lower anchor surface. The connector neck penetrates longitudinally through at least one of a base of the leaflet and an annulus of the heart valve at a manufactured puncture site.

25 Claims, 28 Drawing Sheets

Related U.S. Application Data

(60) Provisional application No. 62/375,146, filed on Aug. 15, 2016.

(52) U.S. Cl.
CPC ............... *A61F 2210/0014* (2013.01); *A61F 2210/0076* (2013.01); *A61F 2220/0008* (2013.01); *A61F 2230/0013* (2013.01); *A61F 2230/0065* (2013.01); *A61F 2230/0095* (2013.01); *A61F 2250/0003* (2013.01); *A61F 2250/0097* (2013.01); *A61F 2250/0098* (2013.01)

(58) Field of Classification Search
USPC .................................................. 623/2.1–2.19
See application file for complete search history.

(56) References Cited

U.S. PATENT DOCUMENTS

| | | | |
|---|---|---|---|
| 5,944,738 A | 8/1999 | Amplatz et al. | |
| 6,123,715 A | 9/2000 | Amplatz | |
| 7,635,386 B1 | 12/2009 | Gammie | |
| 8,709,077 B2* | 4/2014 | Schreck | A61F 2/2433 623/2.18 |
| 8,728,155 B2* | 5/2014 | Montorfano | A61F 2/2409 623/2.18 |
| 9,232,999 B2 | 1/2016 | Maurer et al. | |
| 2002/0107531 A1* | 8/2002 | Schreck | A61B 17/0469 606/142 |
| 2006/0015178 A1 | 1/2006 | Moaddeb et al. | |
| 2006/0229708 A1 | 10/2006 | Powell et al. | |
| 2007/0100439 A1 | 5/2007 | Cangialosi et al. | |
| 2007/0255396 A1 | 11/2007 | Douk et al. | |
| 2008/0039935 A1 | 2/2008 | Buch et al. | |
| 2008/0167714 A1* | 7/2008 | St. Goar | A61B 17/0469 623/2.11 |
| 2008/0234728 A1 | 9/2008 | Starksen et al. | |
| 2009/0043381 A1 | 2/2009 | Macoviak et al. | |
| 2009/0149872 A1 | 6/2009 | Gross et al. | |
| 2010/0137999 A1 | 6/2010 | Shohat | |
| 2011/0046662 A1* | 2/2011 | Moszner | A61B 17/12172 606/213 |
| 2012/0271348 A1 | 10/2012 | Tekulve et al. | |
| 2013/0282114 A1* | 10/2013 | Schweich, Jr. | A61F 2/2445 623/2.19 |
| 2014/0025164 A1* | 1/2014 | Montorfano | A61F 2/2418 623/2.37 |
| 2014/0074223 A1* | 3/2014 | Bonhoeffer | A61F 2/2409 623/1.26 |
| 2014/0114404 A1 | 4/2014 | Gammie et al. | |
| 2014/0257476 A1* | 9/2014 | Montorfano | A61F 2/2409 623/2.38 |
| 2015/0032127 A1 | 1/2015 | Gammie et al. | |
| 2015/0045879 A1* | 2/2015 | Longoria | A61B 17/06 623/2.12 |
| 2015/0196390 A1* | 7/2015 | Ma | A61F 2/2418 623/2.17 |
| 2015/0351904 A1* | 12/2015 | Cooper | A61F 2/2418 623/2.1 |
| 2016/0030176 A1 | 2/2016 | Mohl et al. | |
| 2016/0089234 A1 | 3/2016 | Gifford, III | |
| 2016/0220371 A1 | 8/2016 | Keane | |
| 2016/0235529 A1* | 8/2016 | Ma | A61F 2/2412 |
| 2019/0021852 A1* | 1/2019 | Delgado | A61B 17/00234 |
| 2019/0029814 A1* | 1/2019 | Schweich, Jr. | A61F 2/243 |
| 2019/0076247 A1* | 3/2019 | Zeng | A61F 2/2454 |

FOREIGN PATENT DOCUMENTS

| | | |
|---|---|---|
| WO | 2012/087842 A1 | 6/2012 |
| WO | 2015/061533 A1 | 4/2015 |

* cited by examiner

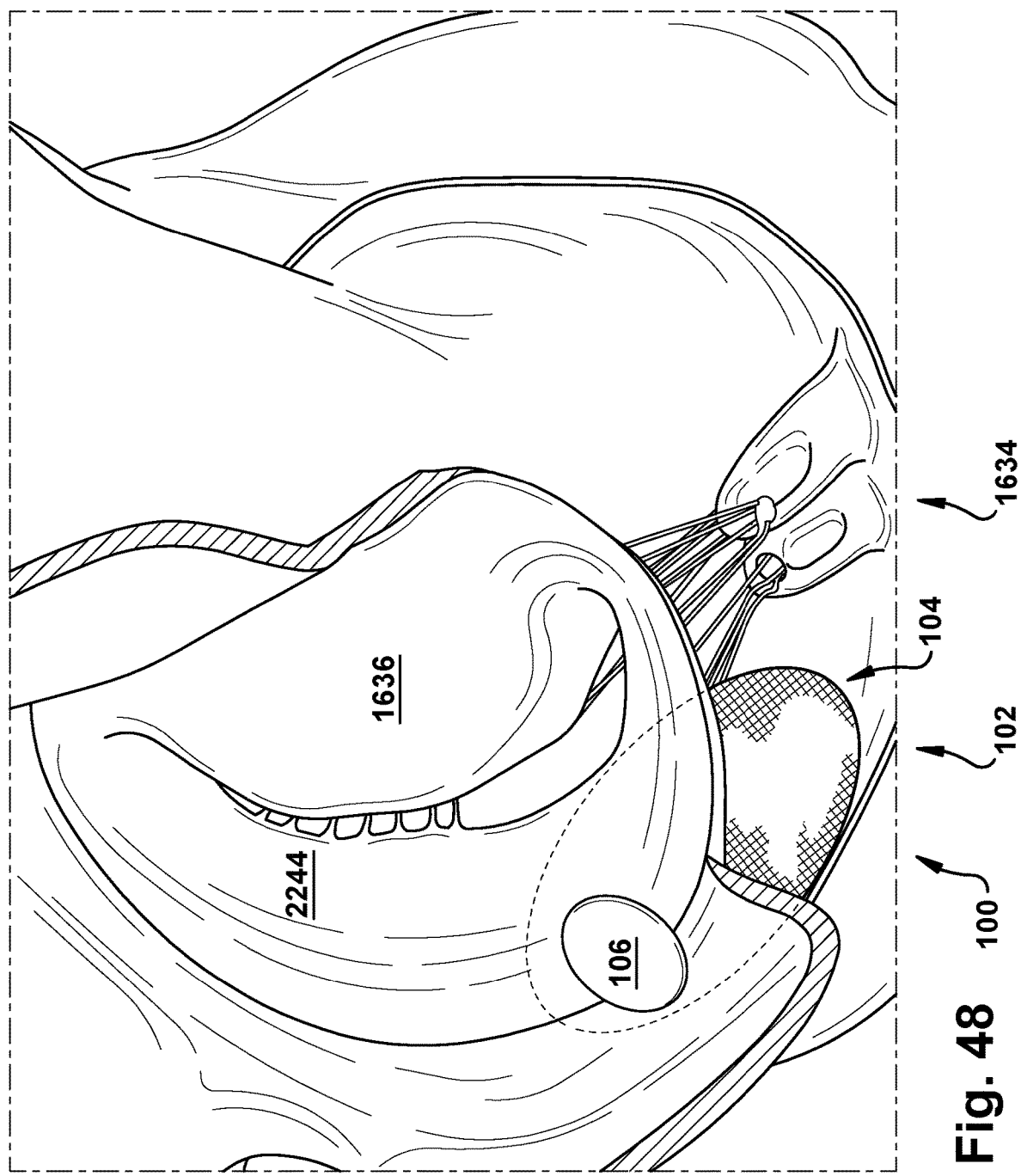

APPARATUSES AND METHODS FOR AT LEAST PARTIALLY SUPPORTING A VALVE LEAFLET OF A REGURGITANT HEART VALVE

RELATED APPLICATION

This application is a divisional of U.S. patent application Ser. No. 15/677,470, filed 15 Aug. 2017, which claims priority from U.S. Provisional Application No. 62/375,146, filed 15 Aug. 2016, the subject matter of both of which is incorporated herein by reference in its entirety.

TECHNICAL FIELD

This disclosure relates to apparatuses and methods for at least partially supporting a valve leaflet of a regurgitant heart valve and, more particularly, to apparatuses and methods for at least partially supporting a valve leaflet of a regurgitant mitral heart valve.

BACKGROUND

Functional Mitral Regurgitation (FMR) and Secondary Tricuspid Regurgitation (STR) are conditions resulting from anatomic dilatation in the shape of the heart caused by ischemia, infarctions, left-sided heart disease, or pulmonary hypertension. FMR and STR are not diseases affecting the cardiac valve leaflets or the valves themselves, but rather involve a ventricle dilation, deformation, and/or displacement which causes the chordae to tether the leaflet and misplaces the normal leaflet coaptation, therefore allowing for bloodflow back into the left or right atrium (i.e., regurgitation). Despite the distinct cause of the regurgitations, many medical interventions still revolve around replacement or repairing the valve with a prosthetic valve or leaflet manipulation, including resection, folding and suturing of the leaflets, clips to pull together the leaflet tissues, and artificial chordae. However, none of these methods have had a desired subvalvular therapeutic effect to date.

SUMMARY

In an aspect, an apparatus for at least partially supporting a leaflet of a regurgitant heart valve is disclosed. The apparatus comprises at least one subvalvular device defining a longitudinal axis and including a subvalvular supporting portion including a leaflet-contacting upper supporter surface longitudinally spaced from an oppositely facing lower supporter surface. A supporter perimeter wall extends longitudinally between, and is integrally and contiguously formed with both of, the upper and lower supporter surfaces. At least a portion of the supporter perimeter wall contacts a subvalvular cardiac wall adjacent to the heart valve. An anchor portion is adjacent to, and longitudinally spaced from, the upper supporter surface. The anchor portion includes a leaflet-contacting lower anchor surface longitudinally spaced from an oppositely facing upper anchor surface. An anchor perimeter wall extends longitudinally between, and is integrally and contiguously formed with both of, the upper and lower anchor surfaces. A connector neck is interposed longitudinally between, and is directly attached to both of, the upper supporter surface and the lower anchor surface. The connector neck penetrates longitudinally through at least one of a base of the leaflet and an annulus of the heart valve at a manufactured puncture site.

In an aspect, a method for at least partially supporting a leaflet of a regurgitant heart valve is provided. A guidewire is placed into a heart of a patient. The guidewire is advanced longitudinally through at least one of a base of the leaflet and an annulus of the heart valve. The guidewire penetrates completely through at least one of a base of the leaflet and an annulus of the heart valve to create a manufactured puncture site. A subvalvular device is provided. The subvalvular device includes a subvalvular supporting portion including a leaflet-contacting upper supporter surface longitudinally spaced from an oppositely facing lower supporter surface. A supporter perimeter wall extends longitudinally between, and is integrally and contiguously formed with both of, the upper and lower supporter surfaces. An anchor portion is adjacent to, and longitudinally spaced from, the upper supporter surface. The anchor portion includes a leaflet-contacting lower anchor surface longitudinally spaced from an oppositely facing upper anchor surface. An anchor perimeter wall extends longitudinally between, and is integrally and contiguously formed with both of, the upper and lower anchor surfaces. A connector neck is interposed longitudinally between, and is directly attached to both of, the upper supporter surface and the lower anchor surface. The subvalvular devices advanced into the heart. The anchor portion is advanced through the manufactured puncture site to a predetermined anchor location on an upper side of the leaflet. The anchor portion is deployed at the predetermined anchor location. The subvalvular device is maintained with the connector neck penetrating longitudinally through at least one of the base of the leaflet and the annulus of the heart valve at the manufactured puncture site. The subvalvular supporting portion is deployed longitudinally adjacent the manufactured puncture site at a location on a lower side of the leaflet, with at least a portion of the supporter perimeter wall contacting a subvalvular cardiac wall adjacent to the valve. At least one of the base of the leaflet in the annulus the heart valve is interposed longitudinally between the anchor portion and the subvalvular supporting portion to locate the subvalvular device in an operating position with respect to the valve. With the subvalvular device, movement of the leaflet during heart operation is resisted to substantially support the leaflet.

In an aspect, an apparatus for at least partially supporting a posterior leaflet of a regurgitant mitral heart valve is provided. The apparatus comprises at least one subvalvular device including a subvalvular supporting portion including a leaflet-contacting upper supporter surface longitudinally spaced from an oppositely facing lower supporter surface. At least one of the upper and lower supporter surfaces includes a convex outer edge and a concave inner edge. A supporter perimeter wall extends longitudinally between, and is integrally and contiguously formed with both of, the upper and lower supporter surfaces. At least a portion of the supporter perimeter wall contacts a subvalvular cardiac wall adjacent to the mitral heart valve concurrently with the concave inner edge coextending with a posterior leaflet. An anchoring feature permanently attaches the subvalvular supporting portion to cardiac tissue such that the subvalvular supporting portion substantially prevents movement of the posterior leaflet during heart function.

In an aspect, an apparatus for at least partially supporting a posterior leaflet of a regurgitant mitral heart valve is provided. The apparatus comprises at least one subvalvular device including a subvalvular supporting portion including a leaflet-contacting upper supporter surface longitudinally spaced from an oppositely facing lower supporter surface. At least one of the upper and lower supporter surfaces includes a convex outer edge and a concave inner edge. A supporter perimeter wall extends longitudinally between, and is integrally and contiguously formed with both of, the upper and lower supporter surfaces. At least a portion of each of the upper and lower supporter surfaces and the supporter perimeter wall is formed from a plurality of radially extending struts which extend substantially parallel to each other along at least a portion of the length thereof. At least a portion of the supporter perimeter wall contacts a subvalvular cardiac wall adjacent to the mitral heart valve concurrently with the concave inner edge coextending with a posterior leaflet. A first anchor portion is adjacent to, and is longitudinally spaced from, the upper supporter surface. The first anchor portion includes a leaflet-contacting lower first anchor surface longitudinally spaced from an oppositely facing upper first anchor surface. A first anchor perimeter wall extends longitudinally between, and is integrally and contiguously formed with both of, the upper and lower first anchor surfaces. A first connector neck is interposed longitudinally between, and is directly attached to both of, the upper supporter surface and the lower first anchor surface. The first connector neck penetrates longitudinally through at least one of the base of the posterior leaflet and the annulus of the mitral heart valve at a manufactured puncture site adjacent an anterior valve commissure. A second anchor portion is adjacent to, and is longitudinally spaced from, the upper supporter surface. The second anchor portion is spaced radially from the first anchor portion. The second anchor portion includes a leaflet-contacting lower second anchor surface longitudinally spaced from an oppositely facing upper second anchor surface. A second anchor perimeter wall extends longitudinally between, and is integrally and contiguously formed with both of, the upper and lower second anchor surfaces. A second connector neck is interposed longitudinally between, and is directly attached to both of, the upper supporter surface and the lower second anchor surface. The second connector neck penetrates longitudinally through at least one of the base of the posterior leaflet and the annulus of the mitral heart valve at a manufactured puncture site adjacent a posterior valve commissure.

BRIEF DESCRIPTION OF THE DRAWINGS

For a better understanding, reference may be made to the accompanying drawings, in which:

FIGS. 38-48 schematically illustrate example steps corresponding to the flowchart of FIGS. 36-37.

DESCRIPTION OF ASPECTS OF THE DISCLOSURE

Figure 1:
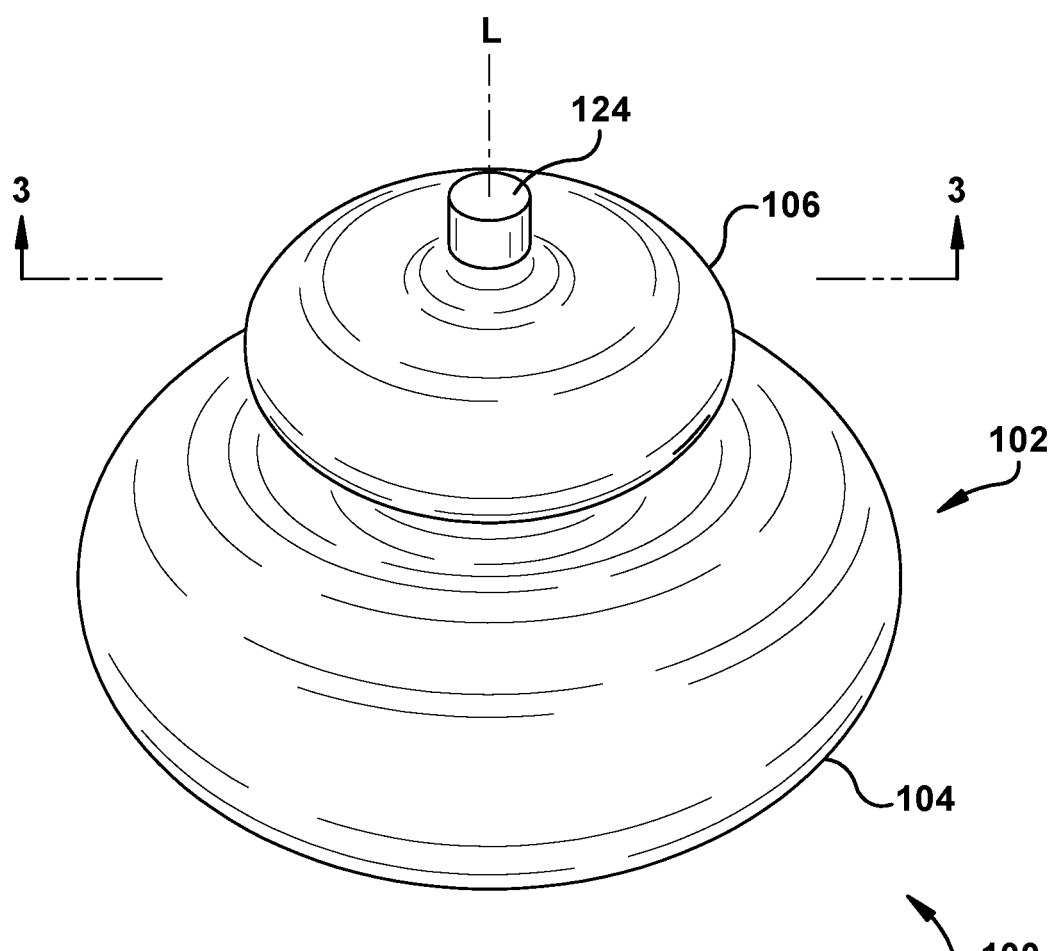
FIG. 1 is a schematic top perspective view of an aspect of the invention.

Unless defined otherwise, all technical and scientific terms used herein have the same meaning as is commonly understood by one of skill in the art to which the present disclosure pertains.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, farm animals, livestock, etc.

As used herein, the terms "treat" or "treating" can refer to therapeutically regulating, preventing, improving, alleviating the symptoms of and/or reducing the effects of FMR and STR. As such, treatment also includes situations where FMR and STR, or at least a symptom associated therewith, is completely inhibited, e.g., prevented from happening or stopped (e.g., terminated) such that the subject no longer suffers from the FMR and STR, or at least the symptom(s) associated therewith.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature might not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

The invention comprises, consists of, or consists essentially of the following features, in any combination. Though the mitral valve is used herein as an example use environment, one of ordinary skill in the art could readily provide a suitable apparatus for use in the tricuspid and/or aortic valves, following the teachings herein.

Aspects of the proposed invention include at least one transcatheter device for percutaneous treatment of patients with FMR and STR, comprising a support system for co-apting cardiac leaflet with the purpose of reducing or eliminating regurgitation leading to reverse remodeling of the ventricular anatomy, which dwells behind the chordae within a subvalvular location, pushing the leaflet (which may be, but is not limited to, a posterior leaflet) from the subvalvular location of the cardiac valve toward the interventricular septum and anterior leaflet. The disclosed invention focuses on correcting the "tipping point" mechanism of the FMR and STR without removing leaflet tissue, placating or deforming the valve annulus, implanting artificial chordae, or transposing native chordae. For FMR and STR, which are characterized by faulty ventricular anatomy and not valve leaflets, the lack of direct leaflet coaptation is particularly relevant and may be the root cause of the regurgitation. One function of the device may be to counter tethering of the valve leaflet by supporting the leaflet.

Devices according to the invention can be fixed or adjustable by mechanical or electromagnetic action during minimally invasive surgery or by transcatheter or percutaneous approach, under echocardiographic and/or fluoroscopy guidance, and also can be provided singly or in multiples, depending on the patient's needs. One goal of this invention is restoring the valve's function instead of removing the leaflet's tissue: "respect rather than resect" using the devices shown and described herein to untether or support the leaflet and thus promote leaflet coaptation of a regurgitant heart valve using a subvalvular support device acting as a prosthesis with a therapeutic effect from the ventricular side.

The device may be at least partially made of a malleable Nitinol or other shape memory alloy material, polyurethane, polytetrafluoroethylene (PTFE), and/or expanded PTFE (ePTFE), or any other material or combination of materials (though it is contemplated that most materials use should be biocompatible) that allows soft deformation or reshaping of the subvalvular apparatus. For most use environments of the present invention, the devices will be stiff enough to withstand further deformation once implanted and subjected to normal physiologic stresses.

The devices can be introduced and delivered under echocardiographic and/or fluoroscopic guidance through a transcatheter or percutaneous approach with a flexible mechanical adjustment catheter transeptally or transfemorally; by transatrial, transapical, transaortic, transcarotid, and/or transsubclavian artery approaches; by open-heart surgery; by robotically assisted surgery; and/or by minimally invasive surgical procedure through direct visualization.

The devices can be fixed to the valve annulus by sutures, hooks, barbs, screw, flexible discs, loop members, bands, rings, adhesives, or any other desired fixation structure or technique to provide adequate support with or without the option for the device to slide or otherwise move relative to these fixation mechanisms. The system can also be supported by one or more additional anchoring mechanisms that are suspended from any of the above structures. The devices may be made at least partially of metal, plastic, elgiloy, Nitinol, stainless steel, titanium, pyrrolitic carbon, any other desired material, and/or any combination thereof, and can be covered with synthetic, biological, and/or biocompatible materials. When the devices include an expandable balloon, that balloon can be made of any desired material and can be inflated with saline, a polymer, physiologically triggered material that hardens over time to create a fixed structure, any other suitable material, and or any combination thereof. The devices also can be coated and/or impregnated with one or more pharmacologic and/or biologic agents, for immediate and/or time release provision of the agents to the surrounding tissue.

The devices of the present invention may act to normalize and remodel the leaflet shape and function, correct the leaflet mobility, coapted by improving the leaflet closure movement during systole, and corrects the unbalance angle of leaflet coaptation and sub-valvular apparatus position for valve regurgitation, without removing leaflet tissue, chordal shortening, transposing or replacement, placating and deforming the valve annulus, or using other surgical techniques or sophisticated procedures for making the valve competent. The devices can be adjustable depending on the anatomic leaflet and sub-valvular apparatus configuration, to obtain normal correction by mechanical or electromagnetic adjustment through a flexible catheter by echo guidance. This adjustment could be accomplished, for example, under echocardiographic and/or fluoroscopic guidance through a transcatheter or percutaneous approach with a flexible mechanical adjustment catheter transeptally or transfemorally; by transatrial, transapical, transaortic, transcarotid, and/or transsubclavian artery approaches; by open-heart surgery; by robotically assisted surgery; and/or by minimally invasive surgical procedure through direct visualization.

The devices of the present invention, including at least one subvalvular mitral spacer device described below, can be implanted and anchored as an independent single device at the level of P1, P2, and/or P3 mitral leaflets, as well as in analogous positions for the anterior, septal, and/or posterior tricuspid leaflets. It is also contemplated that the devices could be adjusted, removed, and/or replaced with other devices in a separate surgical procedure, accomplished at a different time than the initial implantation surgical procedure.

Below is a description of an implantable device placed within the subvalvular space and mechanically supporting a lull and tethered mitral valve leaflet due to an ischemic event. The device is placed between the ventricular surface of the posterior leaflet and the left ventricle posterior wall location—i.e., under the leaflet in the ventricular space and on the posterior wall location. Transfemoral retrograde approach may be utilized, whereby the access is through the femoral artery and device navigated across the aortic valve in the left ventricle. The device may have an anchoring mechanism, with single and/or multiple anchors perforating the mitral annulus at the level of P1, P2, and/or P3 from the ventricular to the atrial direction.

The device may be anchored to the valve annulus, deployed, and functionally tested within a beating heart. Responsive to the size of the valve, amount of regurgitation present, or any other desired factors, the user might elect to deploy single or multiple devices for a particular patient. The device may be built with an adjustment mechanism allowing it to have different shapes to help increase the coaptation surface between the posterior and anterior leaflets. The device may be designed to remain for the entire patient's life span. Features of the device include:

Delivery system for location "management". This element assists a physician in navigating to a desired location and orienting a vector pointing from the ventricle toward the atrium. The delivery system is a lumen allowing other devices to be channeled if desired. For example, a preliminary or "sizer" device (such as, but not limited to, a compliant balloon) could be inflated or otherwise deployed in the subvalvular place to locate a desired anchor location and/or pre-implant assessment of efficacy before implantation.

Puncture mechanism. The catheter may include a puncture mechanism to go from the ventricle to the atrium side without creating regurgitation or a significant tear to the valve annulus.

Anchor management. This element helps to facilitate anchors being navigated through the delivery system, and deployed in the atrial side with a connection to another structure located in the ventricular side. The anchors may be temporarily positioned until the physician is satisfied with the location before permanently anchoring the device. The anchor mechanism may be atraumatic to the body.

The devices according to the present invention may assist with reducing or eliminating cardiac valve regurgitation by pushing or moving forward the tethering posterior leaflet and increasing the surface of leaflet coaptation between the posterior and the anterior leaflet. To achieve this purpose, a repositionable and retrievable sub-valvular structure may be anchored onto a specific anatomy of the mitral annulus such as P1, P2, and/or P3 leaflet scallop levels.

The "repositionable" and "retrievable" attributes could be interpreted as follows. Repositionability may be a desired feature to adjust the location of the devices in situ as to tune its anatomical position to achieve an increased leaflet surface co-aptation. The repositionable feature will often be carried out before any permanent or semi-permanent anchor mechanism is deployed, which can be considered a "coarse repositioning".

Once the anchor is deployed, the device may have the ability to engage in a "fine repositioning" as the last in situ adjustment to achieve the desired functionality.

Retrieveability may be a desired feature to remove the device from the ventricle. During implantation procedure, if the device is not performing as intended, it could then be collapsed and retrieved immediately. During functional testing after implantation, if the device is not sized properly and does not achieve the intended performance, it could be removed after the anchor has been deployed. In this case, the structure is retrieved and the anchor safely removed if possible, otherwise the anchor may be "safely buried". During chronic or long-term follow-up and/or under extremely urgent conditions, it may be possible to surgically or percutaneously remove the device.

Some example features of a device according to the present invention include:

The ability to be delivered in a retrograde fashion through a transfemoral access. The catheter will go through a beating aortic valve and flex toward the ventricular side of mitral valve annulus.

A catheter profile size of at least about eight French (8 Fr) and optionally about eighteen French (18 Fr), for many use environments.

A stent structure constructed, for example, from braided Nitinol wires. The stent structure could be configured to produce a desired radial force (no matter the type of construction). If the radial force is maintained, the device could be "one-size-fits-all". As another option, various sizes of the device could be provided, such as small, medium, and large.

The device may be PTFE coated or covered with some anti-thrombogenic coating such as heparin-based coating.

The device design could account for thrombus reduction through minimizing shear stresses around the device and avoiding any accumulation or blood pooling locations.

The device could anchor onto P1, P2, and/or P3.

The device could be placed with one or more of the following, or any other suitable, image modalities, and/or any other suitable imaging technologies: Fluoroscopy, which may be helpful with catheter navigation and device placement prior to device anchoring; Transesophageal echocardiogram, or TEE, for help with anchoring; and Intracardiac echocardiography (ICE).

The device may be deployed and repositioned in any desired manner, including but not limited to (1) Device is deployed first (without any anchoring) and functional performance is assessed prior to deploying the first anchor. In case clinical performance is poor, the device could be retrieved and procedure aborted; and (2) First, an anchor is deployed, followed by the device. Should the performance be poor, then the device is recovered and the initially placed anchor may be either left behind or retrieved.

The device may be retrievable during the initial implantation procedure until released by the physician at the end of the implantation procedure. Optionally, the device may be retrievable and/or repositionable in a later surgical procedure.

Description of Aspects of the Invention with Reference to the Figures

Figure 2:
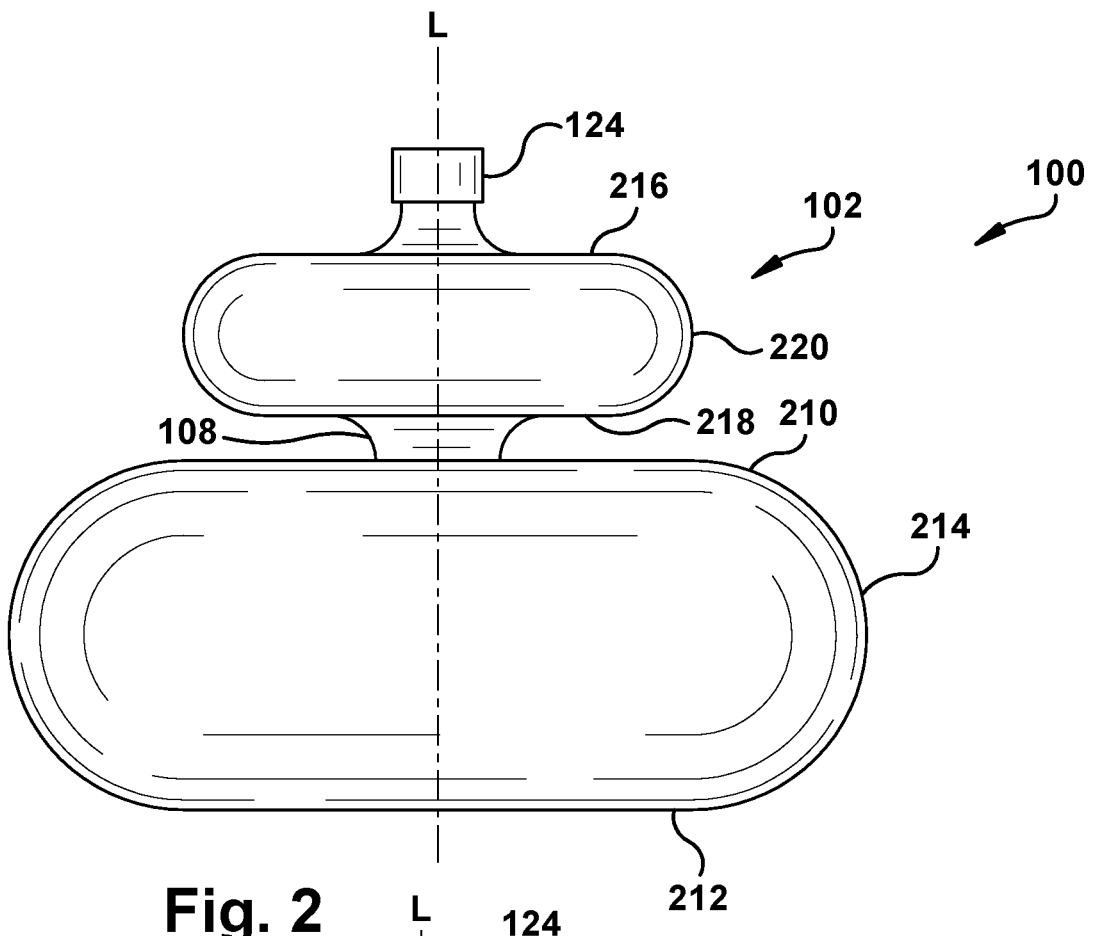
FIG. 2 is a schematic side view of the aspect of FIG. 1.
Figure 3:
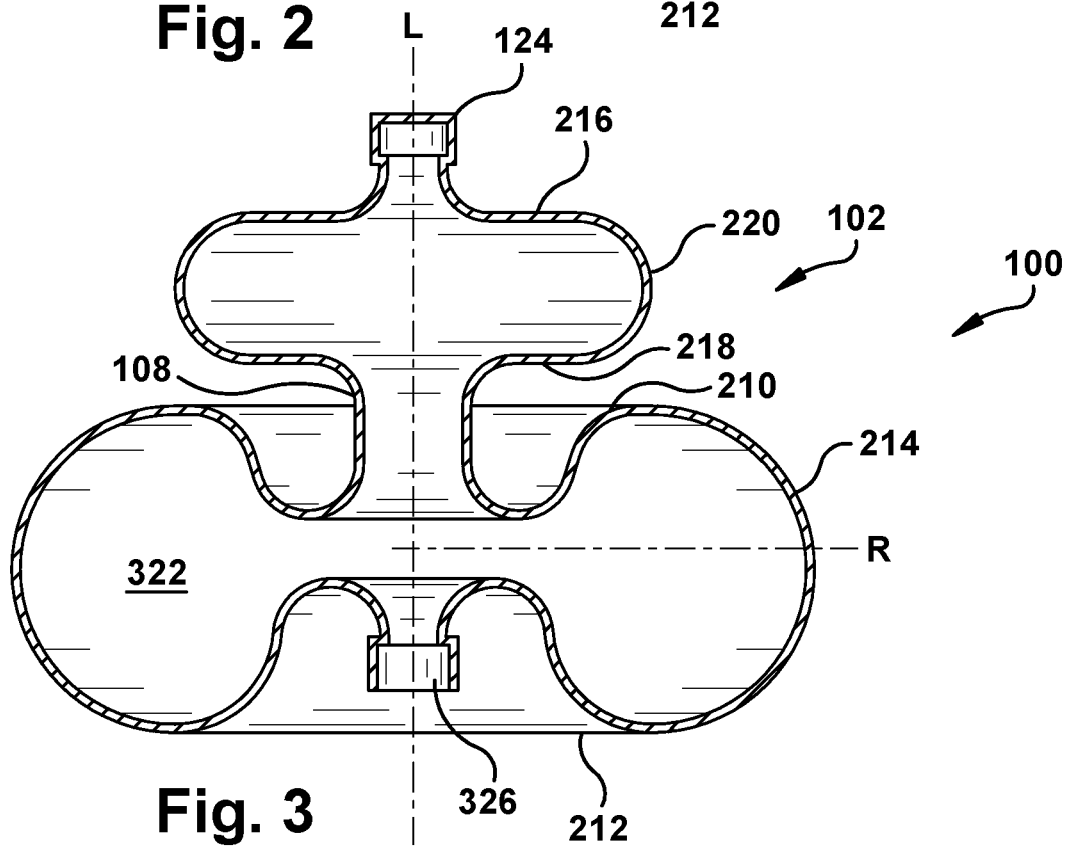
FIG. 3 is a cross-sectional view taken along line 3-3 of FIG. 1.
Figure 4:
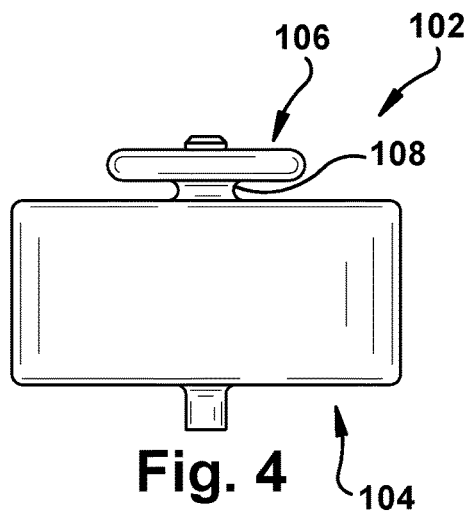
FIGS. 4-10 are schematic side views of various example configurations of the aspect of FIG. 1.
Figure 5:
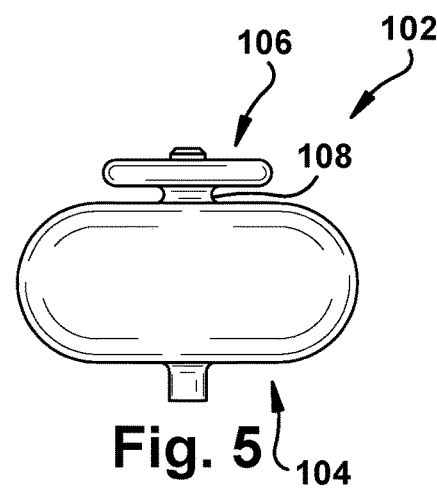

FIGS. 1-15 depict a first embodiment of an apparatus 100 for at least partially supporting a heart valve leaflet, such as a posterior leaflet of a regurgitant mitral heart valve. The apparatus 100, as shown in FIGS. 1-3 includes at least one subvalvular device 102 defining a longitudinal axis L and including a subvalvular supporting portion 104, an anchor portion 106 (e.g., an atrially-located anchor portion 106), and a connector neck 108. The term "longitudinal" is used herein to indicate a direction substantially perpendicular to the longitudinal axis L, such as the vertical direction in the orientation of at least FIGS. 2-3.

Turning now to FIG. 2, the subvalvular supporting portion 104 includes a leaflet-contacting upper supporter surface 210 longitudinally spaced from an oppositely facing lower supporter surface 212. A supporter perimeter wall 214 extends longitudinally between the upper and lower supporter surfaces 210 and 212. The supporter perimeter wall 214 is integrally and contiguously formed with both of the upper and lower supporter surfaces 210 and 212. As used herein, the phrase "is integrally and contiguously formed with" indicates a situation wherein the structures described as such are manufactured and used as a single piece, not assembled from subcomponents. When the subvalvular device 102 is in an operating position with respect to the heart valve, at least a portion of the supporter perimeter wall 214 contacts a subvalvular cardiac wall adjacent to the heart valve annulus.

One of ordinary skill in the art will understand that the upper and lower supporter surfaces 210 and 212, as well as the supporter perimeter wall 214, can have any desired dimensions and shapes. In the subvalvular device 102 shown in FIGS. 1-3, the supporter perimeter wall 214 extends somewhat continuously with the upper and lower supporter surfaces 210 and 212, due to the relative curvatures of those surfaces. For a particular use environment of the apparatus 100, it is even contemplated that the supporter perimeter wall 214 could be extremely narrow, almost linear, and define an inflection point between the upper and lower supporter surfaces 210 and 212 along the side contour of the subvalvular supporting portion 104.

The anchor portion 106 is adjacent to, and longitudinally spaced from, the upper supporter surface 210. The anchor portion 106 includes a leaflet-contacting lower anchor surface 218 longitudinally spaced from an oppositely facing upper anchor surface 216. An anchor perimeter wall 220 extends longitudinally between the upper and lower anchor surfaces 216 and 218. The anchor perimeter wall 220 is integrally and contiguously formed with both of, the upper and lower anchor surfaces 216 and 218.

One of ordinary skill in the art will understand that the upper and lower anchor surfaces 216 and 218, as well as the anchor perimeter wall 220, can have any desired dimensions and shapes. In the subvalvular device 102 shown in FIGS. 1-3, the anchor perimeter wall 220 extends somewhat continuously with the upper and lower anchor surfaces 216 and 218, due to the relative curvatures of those surfaces. For a particular use environment of the apparatus 100, it is even contemplated that the anchor perimeter wall 220 could be extremely narrow, almost linear, and define an inflection point between the upper and lower anchor surfaces 216 and 218 along the side contour of the anchor portion 106.

A connector neck 108 is interposed longitudinally between, and directly attached to both of, the upper supporter surface 210 and the lower anchor surface 218. When the subvalvular device 102 is in an operating position with respect to the heart valve, the connector neck 108 penetrates longitudinally through the valve annulus (e.g., a mitral valve annulus) and/or a base of the posterior leaflet at a manufactured puncture site. The term "manufactured puncture site" is used herein to reference an artificially created, not naturally occurring (congenital or otherwise), opening in the patient tissue which is created and used specifically in conjunction with the apparatus 100.

As shown in FIG. 3, the subvalvular supporting portion 104, anchor portion 106, and connector neck 108 may collectively enclose a single contiguous interior volume 322. This may be particularly desirable when at least a portion of the subvalvular device 102 is a balloon.

The subvalvular device 102 may include, as shown in FIGS. 1-3, at least one of a top cap 124 and a bottom cap 326. When present, the top and bottom caps 124 and 326 may protrude away from the connector neck 108 in the longitudinal direction from the upper anchor surface 218 and lower supporter surface 212, respectively, or may be recessed into those respective surfaces. When the subvalvular device 102 is at least partially formed of a braided structure, the top and/or bottom caps 124 and 326 may serve to hold the braided structure together at the termination points thereof. The top and bottom caps 124 and 326 can have any desired structure and can be provided for any desired reason, such as, but not limited to, selective attachment to one or more structures that aid in delivery and placement of the apparatus 100. For example, if the subvalvular device 102 includes a balloon, the top and/or bottom caps 124 and/or 326 could be configured to selectively interface with an inflation fluid source. Optionally, the top and/or bottom caps 124 and 326 could serve a "marker band" function, in that, when these caps are radiopaque, they can serve to assist with placement of the device. It is also contemplated that one or more other radiopaque markers (not shown) could be placed in any desired position with respect the apparatus 100, to assist with achieving a desired placement thereof.

As present in the embodiment of FIGS. 1-3, both of the upper and lower supporter surfaces 210 and 212 may include a longitudinally varying contour along a radial dimension thereof. The "radial" direction, as referenced herein, is substantially perpendicular to the longitudinal direction, and is the horizontal direction, in the orientation of at least FIGS. 2-3. The contours of the upper and lower supporter surfaces 210 and 212 are substantially mirrored with respect to each other about a radially-oriented plane R. As shown particularly in FIG. 3, the upper and lower supporter surfaces 210 and 212 and supporter perimeter wall 214 may collectively define a substantially torus-shaped subvalvular supporting portion 104. A "torus", as used herein, is a doughnut-shaped surface generated by a circle rotated about an axis in its plane that does not intersect the circle. A torus-shaped subvalvular supporting portion 104 has been found by the inventors to exhibit particular, potentially desirable mechanical properties when the subvalvular device 102 is in the operating position. For example, the torus-shaped subvalvular supporting portion 104, when made of certain materials, has a tendency to transform from at least partially flexible to substantially rigid under pressure. Therefore, when the heart is beating, a torus-shaped subvalvular supporting portion 104 may be helpful in resisting motion of a valve leaflet with which it is associated. This torus-shaped subvalvular supporting portion 104 may thus help improve antegrade motion of the valve leaflet via an "untethering" function to create a competent mitral valve function by substantially eliminating mitral regurgitation.

Figure 6:
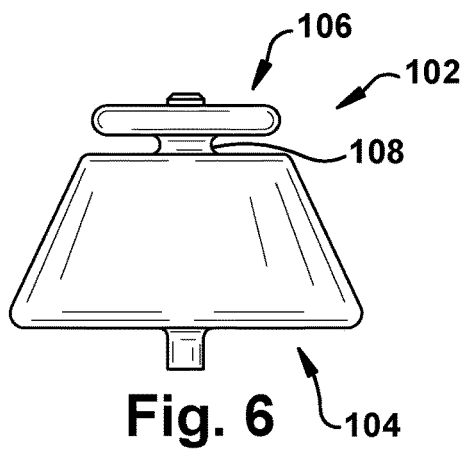

However, it is contemplated that the subvalvular device 102, and portions thereof, could have any desired configuration. For example, and as shown in the subvalvular devices 102 of FIGS. 4-10, both of the upper and lower supporter surfaces 210 and 212 could be substantially planar and mutually parallel. More specifically, it is contemplated that the subvalvular supporting portion 104 could be substantially circularly symmetrical about the longitudinal axis L. The term "circularly symmetrical" is used herein to reference a type of continuous symmetry for a planar object that can be rotated by any arbitrary angle and map onto itself. The subvalvular supporting portion 104, when viewed from the radial direction, could have a profile substantially in the shape of at least one of a rectangle (FIG. 4), an oval (FIG. 5), and a trapezoid (FIG. 6).

As another option, and as shown in FIGS. 20-25, when viewed from the radial direction, the subvalvular supporting portion 104 may have a profile substantially in the shape of a rectangle, but, when viewed from the longitudinal direction, the subvalvular supporting portion 104 may have a profile substantially in the shape of an ellipse. Thus, the subvalvular supporting portion 104 could be shaped like an elliptical cylinder, for certain use environments of the present invention.

Figure 7:
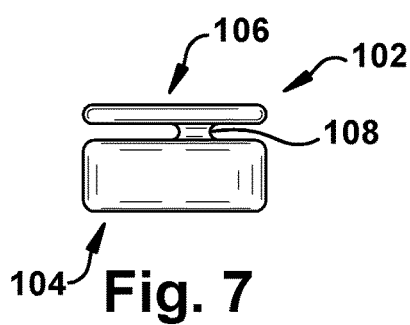
Figure 8:
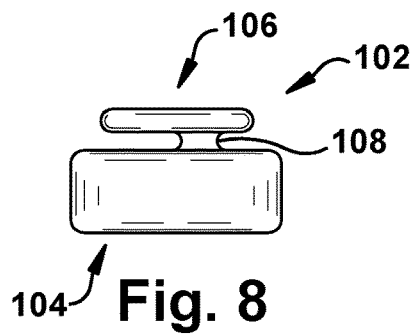
Figure 9:
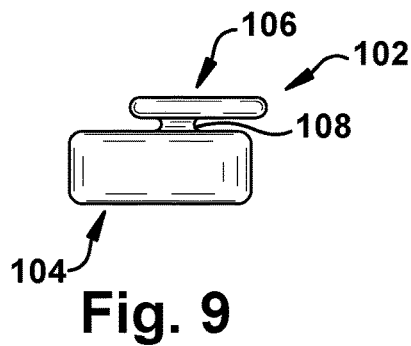
Figure 10:
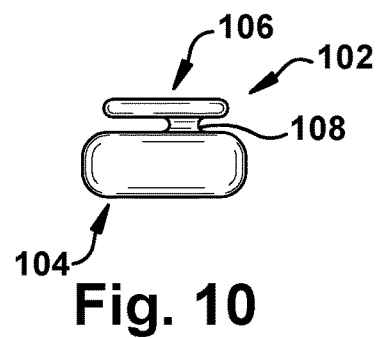

The subvalvular supporting portion 104 and the anchor portion 106 could have any of a number of different configurations, both absolute and relative. Several of these example configurations are shown in FIGS. 7-10, though these figures, like all figures in the present application, are not drawn to scale. (It should be understood that the anchor portion 106 and the subvalvular supporting portion 104 themselves could have any desired shape or profile, but are shown as being disk-shaped and cylindrical, respectively, for the sake of example.) The anchor portion 106 could have a maximum radial dimension (i.e., a maximum measurement in the radial direction R) that is larger than a maximum radial dimension of the subvalvular supporting portion 104. As shown in FIG. 7, the anchor portion 106 could have a maximum radial dimension that is the same as a maximum radial dimension of the subvalvular supporting portion 104. As shown in FIGS. 8-10, the anchor portion 106 could have a maximum radial dimension that smaller than a maximum radial dimension of the subvalvular supporting portion 104.

The subvalvular supporting portion 104, connector neck 108, and anchor portion 106 could also have any desired relative positions in the radial direction. For example, as shown in the subvalvular devices 102 of FIGS. 1-6, the subvalvular supporting portion 104 and the anchor portion 106 can both be substantially circularly symmetrical about the connector neck 108. Instead, as shown in FIGS. 7-10, at least one of the subvalvular supporting portion 104 and the anchor portion 106 can be circularly asymmetrical with respect to the connector neck 108. That is, the subvalvular supporting portion 104 and/or the anchor portion 106 could be "offset" in the radial direction from the connector neck 108. This may be desirable for a particular patient's heart structure arrangement. For many use environments of the apparatus 100 it will be desirable to have the anchor portion 106 in close proximity to an atrial wall, for example. To achieve desired placement of the apparatus 100, one of ordinary skill in the art can readily configure a subvalvular device 102 having a subvalvular supporting portion 104, a connector neck 108, an anchor portion 106 with any desired longitudinal and radial shapes, dimensions, relative arrangements, or other configurations.

Figure 11:
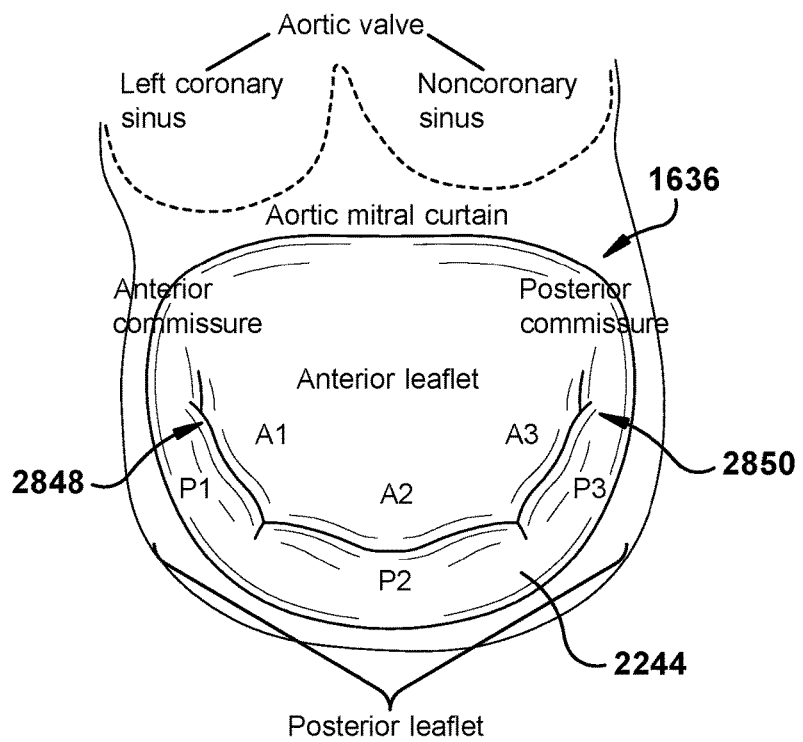
FIG. 11 is an anatomical depiction of a mitral valve of a patient.

FIG. 11 is a labeled anatomic drawing of a mitral valve portion of a heart, taken from above, and these structures will be referenced herein.

Figure 12:
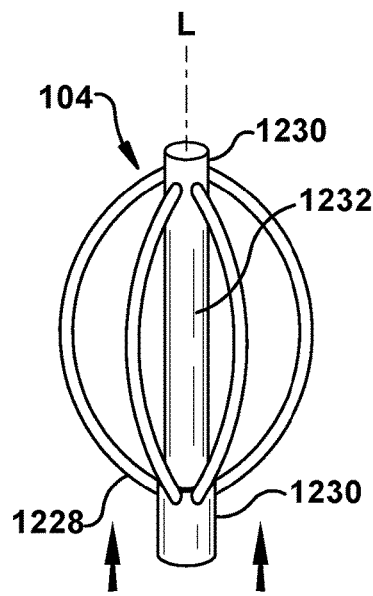
FIGS. 12-14 illustrate a sequence of operation of an example configuration of the aspect of FIG. 1.
Figure 13:
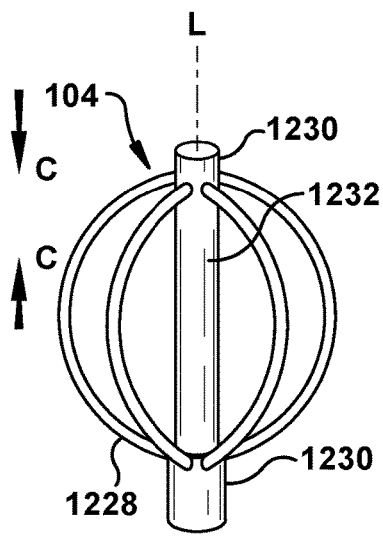
Figure 14:
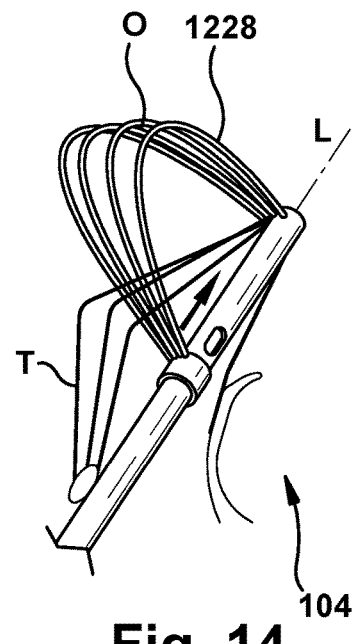

As shown in FIGS. 12-14, at least one of the subvalvular supporting portion 104 (shown here) and the anchor portion 106 may be substantially formed of a plurality of longitudinally oriented struts 1228, arranged radially with respect to the longitudinal axis L. A body portion of each strut 1228 is selectively bowed radially outward from the longitudinal axis L, during transformation of the subvalvular supporting portion 104 from a transport position (T, in FIG. 14) to an operating position (O, in FIG. 14). For example, and as shown in the sequence from FIGS. 12-13, the struts 1228 could be subject to a compressive force C in the longitudinal direction. When both ends of the struts 1228 are anchored, such as via hubs 1230 to a central shaft 1232, the central portions of the struts 1228 will thereby splay outward in a "cocktail umbrella" type manner and can be "locked" there to provide a three-dimensional construct which serves the function of at least one of the subvalvular supporting portion 104 and an anchor portion 106.

It should be noted that the version of the subvalvular supporting portion 104 shown in FIG. 14 has struts 1228 which only surround a portion of the longitudinal axis L, in contrast to the substantially 360° surrounding of the longitudinal axis L in FIGS. 12-13 by the struts 1228. FIG. 14 therefore represents another potential asymmetrical configuration of a subvalvular supporting portion 104, which could be accomplished with the strut 1228 arrangement shown in that figure, or with any other configuration or embodiment of the subvalvular supporting portion 104.

Figure 15:
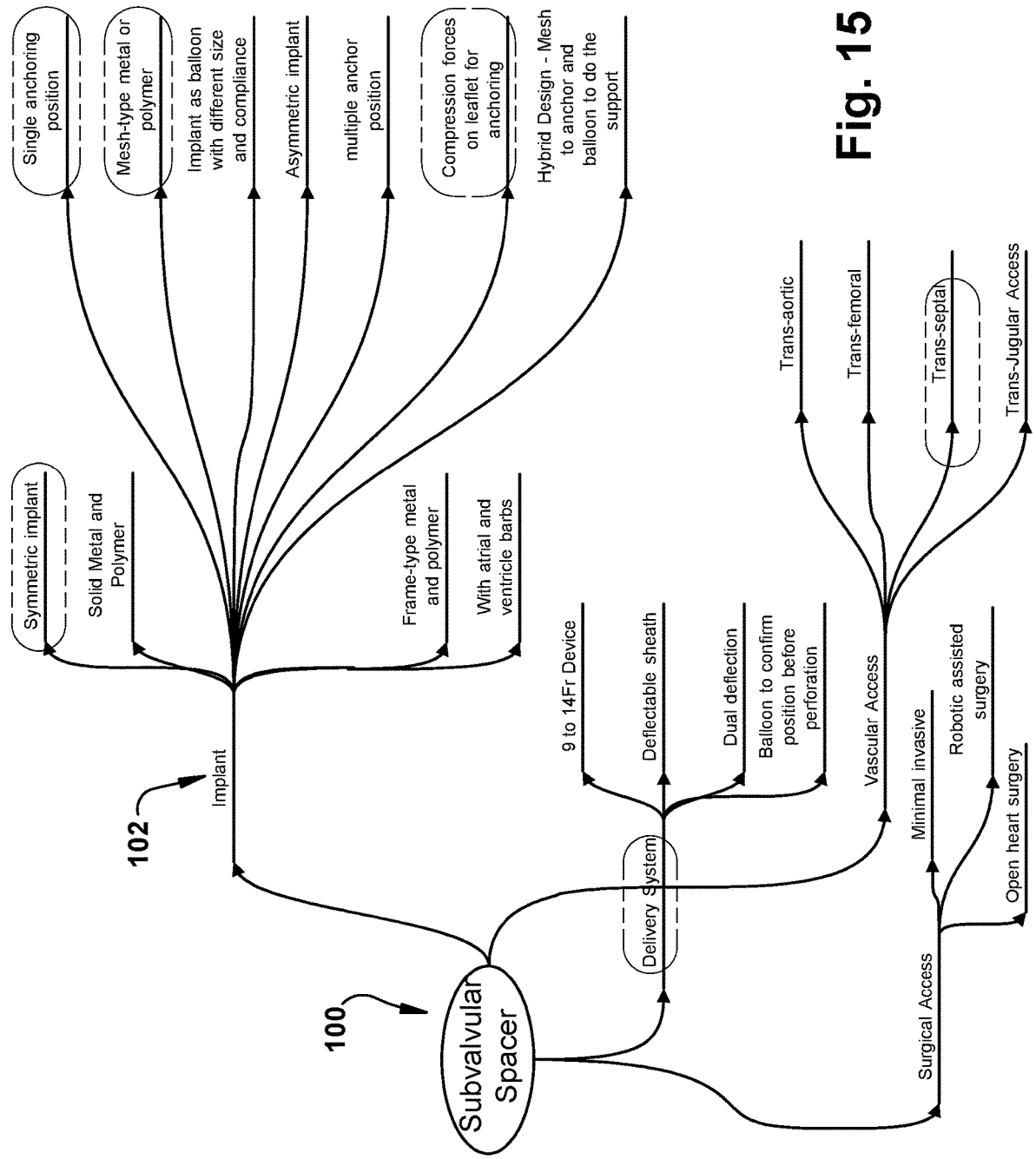
FIG. 15 verbally describes various features of example aspects of the invention.
Figure 16:
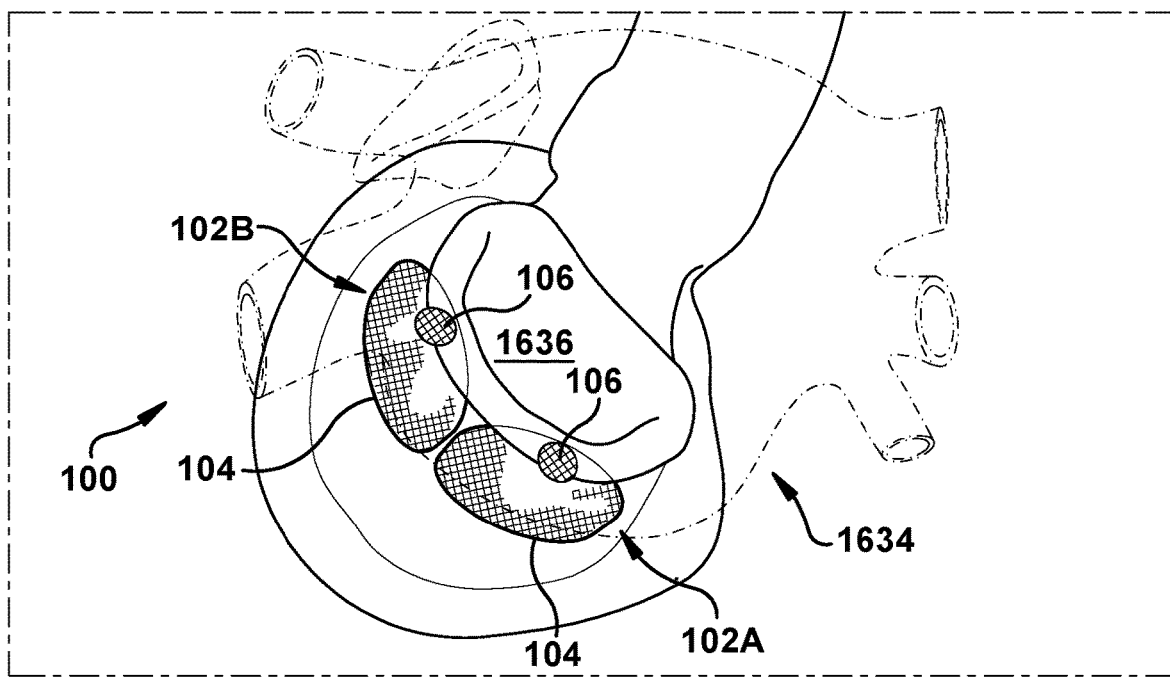
FIG. 16 is a partial top perspective view of an aspect of the invention.
Figure 17:
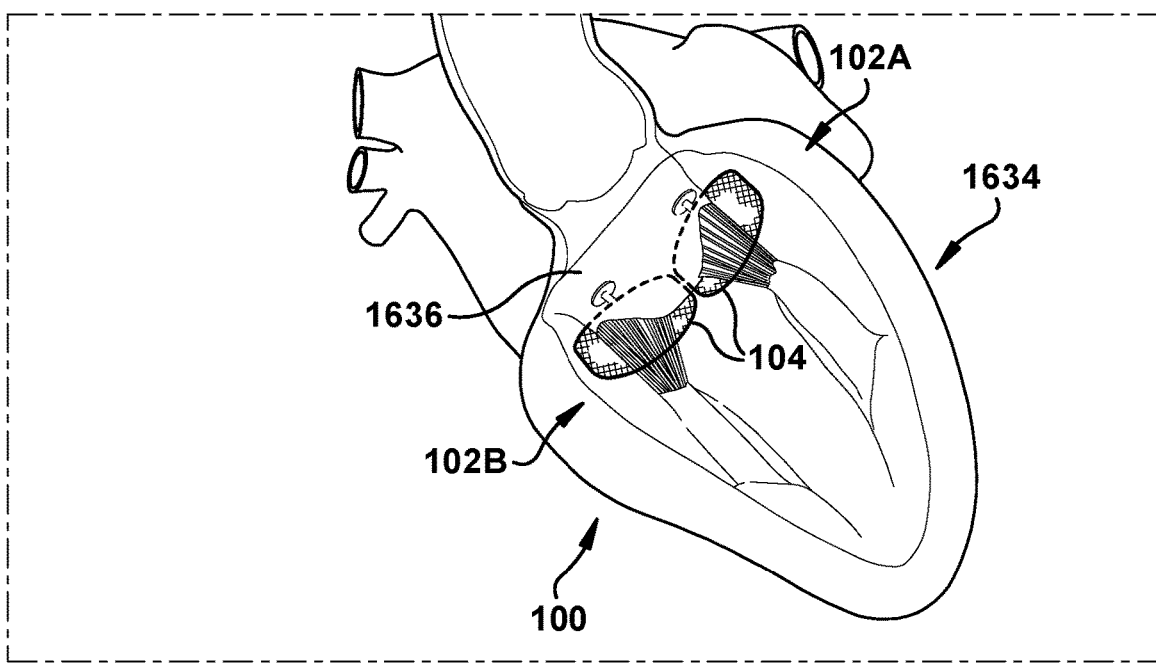
FIG. 17 is a partial side perspective view of the aspect of FIG. 16.
Figure 18:
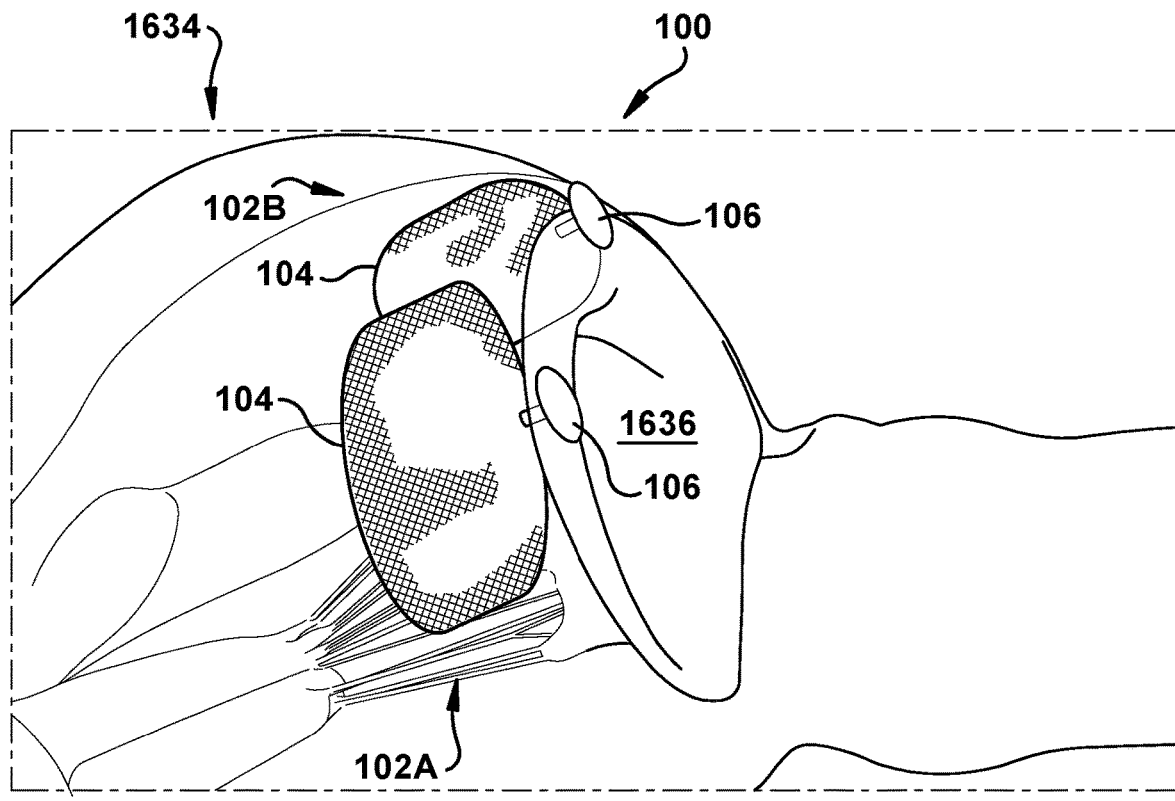
FIG. 18 is a partial side perspective view of the aspect of FIG. 16.
Figure 19:
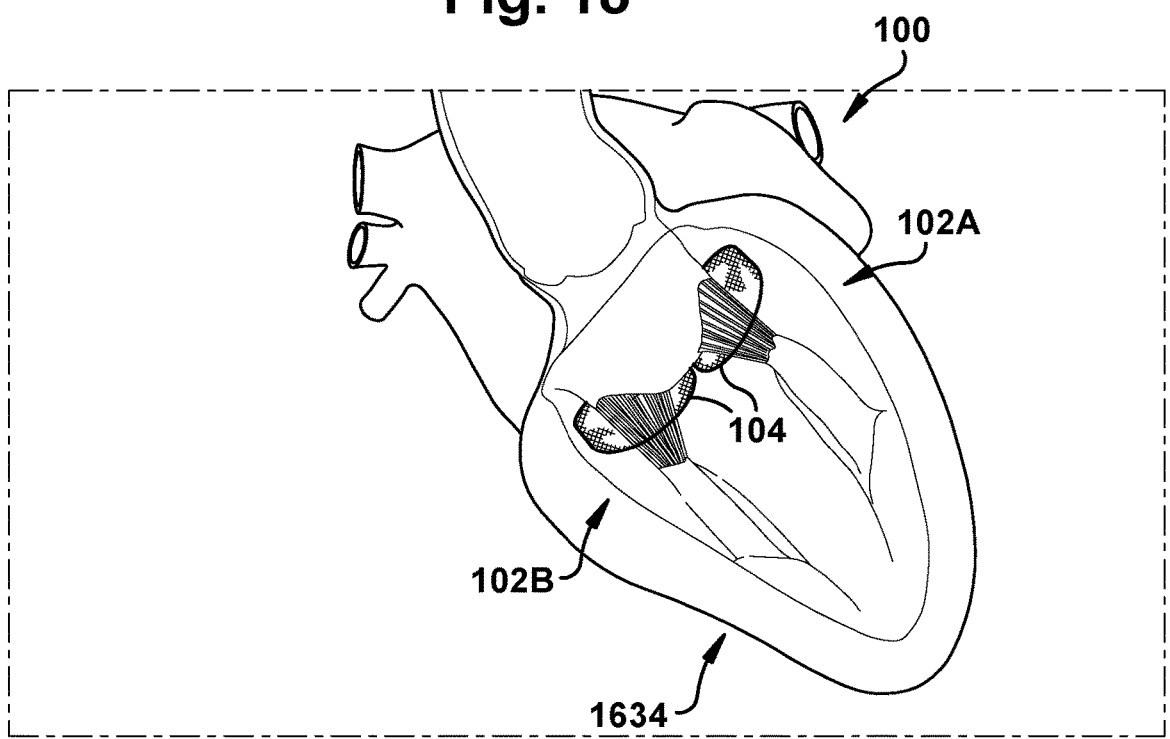
FIG. 19 is a partial bottom perspective view of the aspect of FIG. 16.
Figure 20:
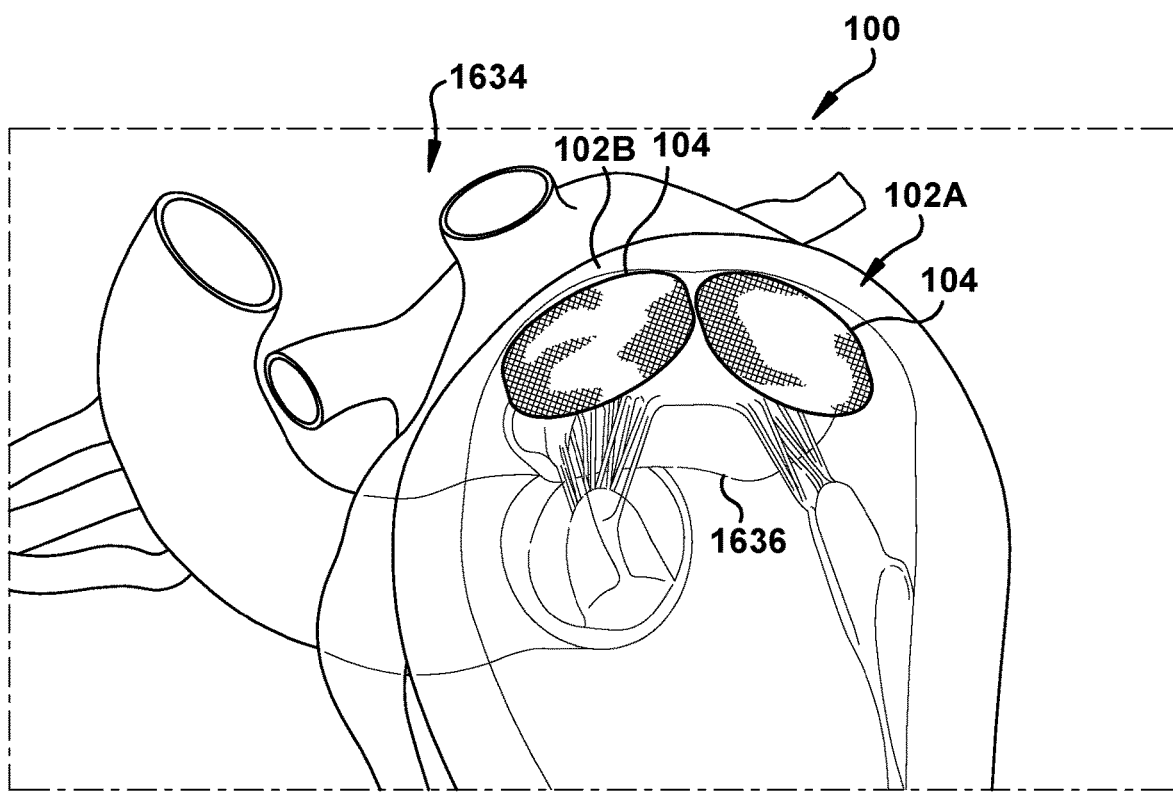
FIG. 20 is a partial bottom perspective view of the aspect of FIG. 16.
Figure 21:
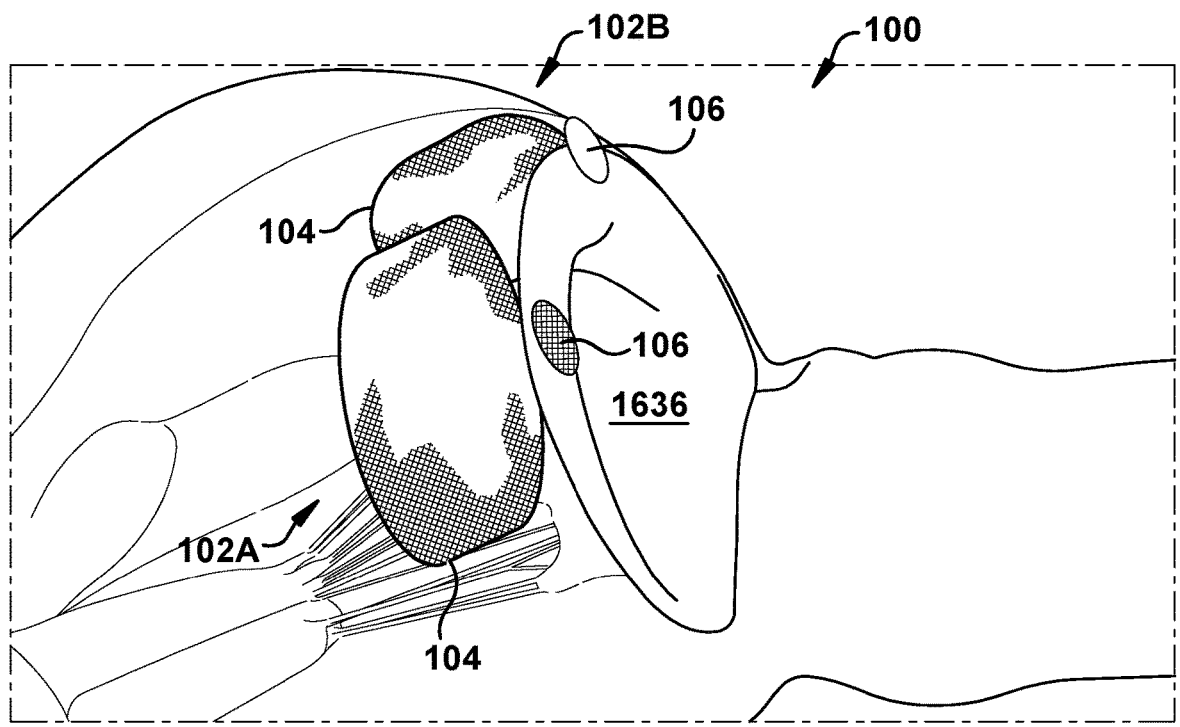
FIG. 21 is a partial side perspective view of the aspect of FIG. 16.
Figure 22:
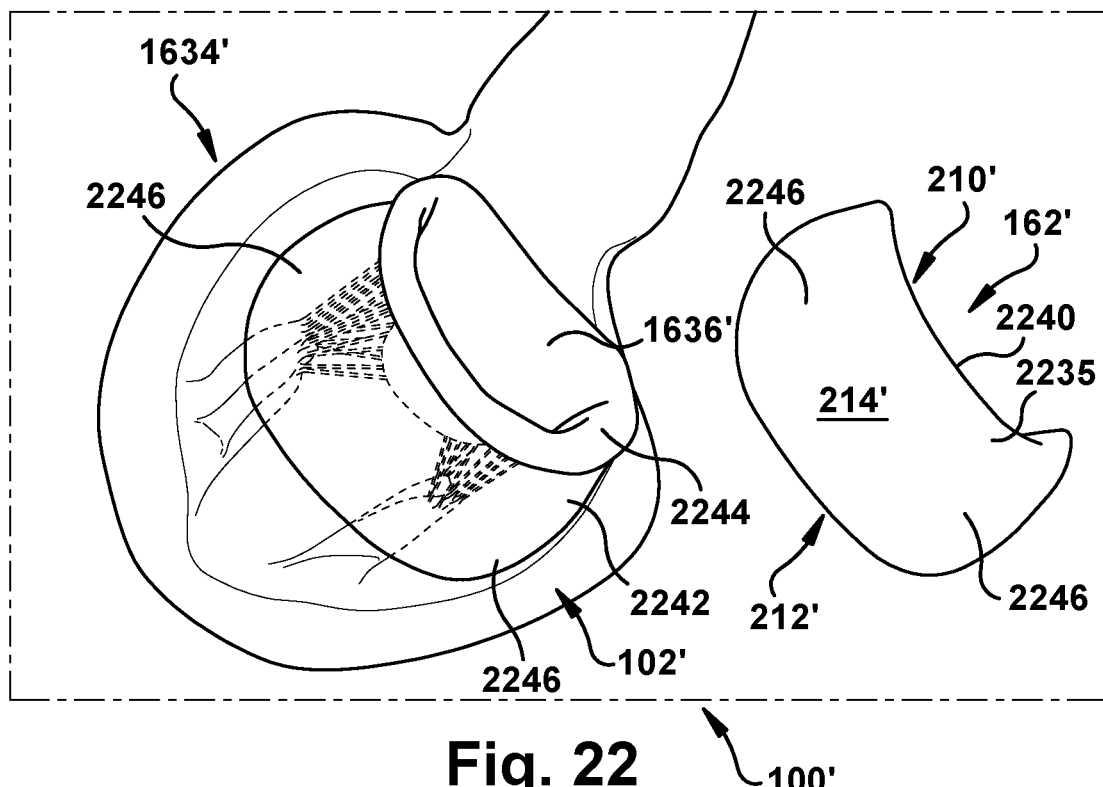
FIG. 22 is a partial side perspective view of an aspect of the invention, both inside and outside an example use environment.
Figure 23:
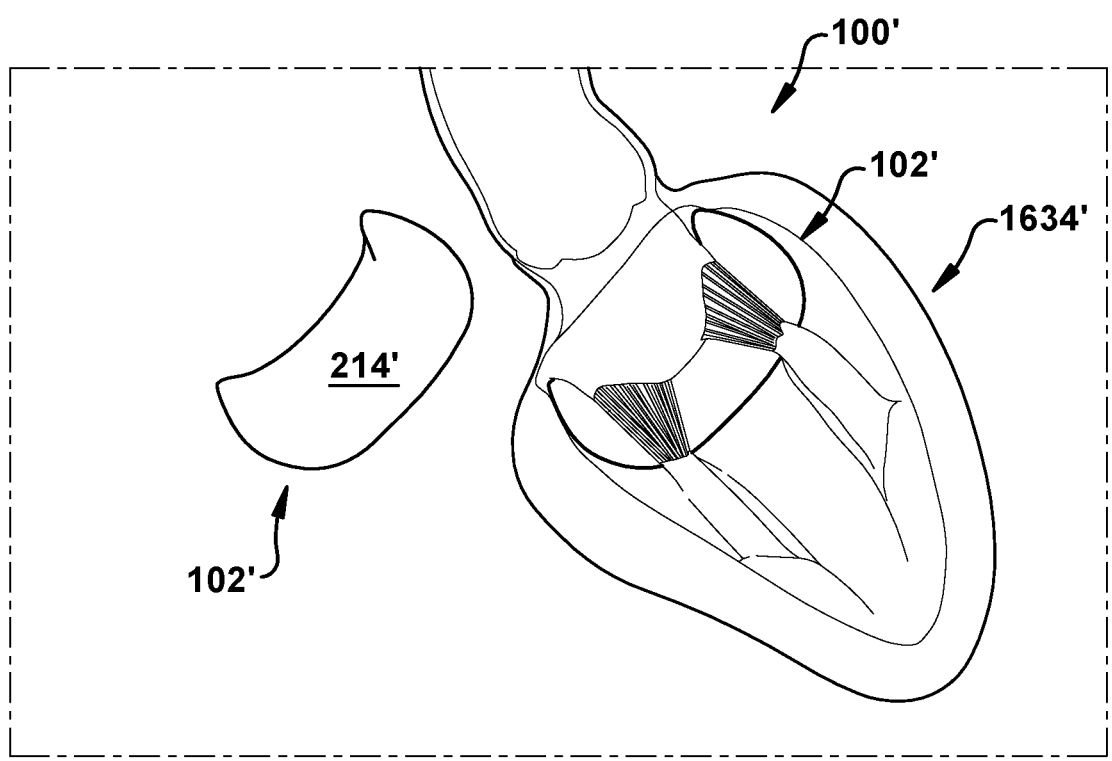
FIG. 23 is a partial bottom perspective view of the aspect of FIG. 22, both inside and outside the example use environment.
Figure 24:
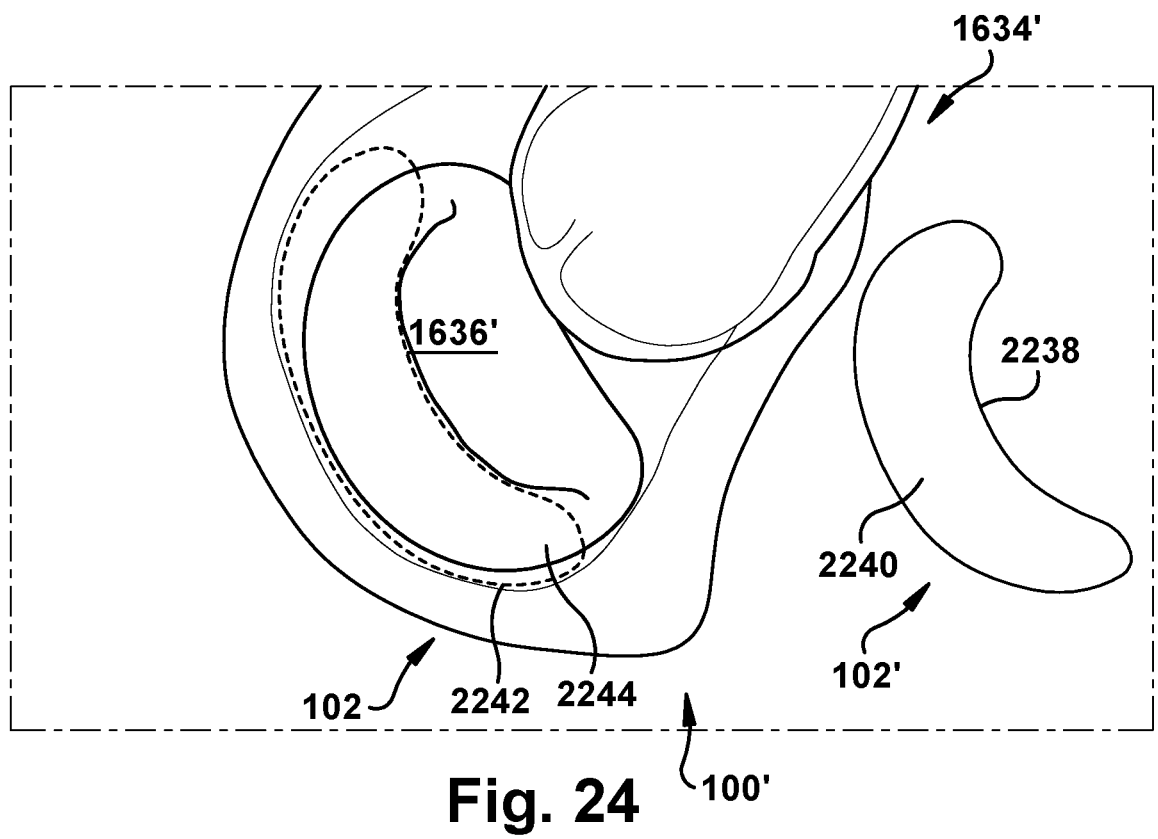
FIG. 24 is a partial top perspective view of the aspect of FIG. 22, both inside and outside the example use environment.
Figure 25:
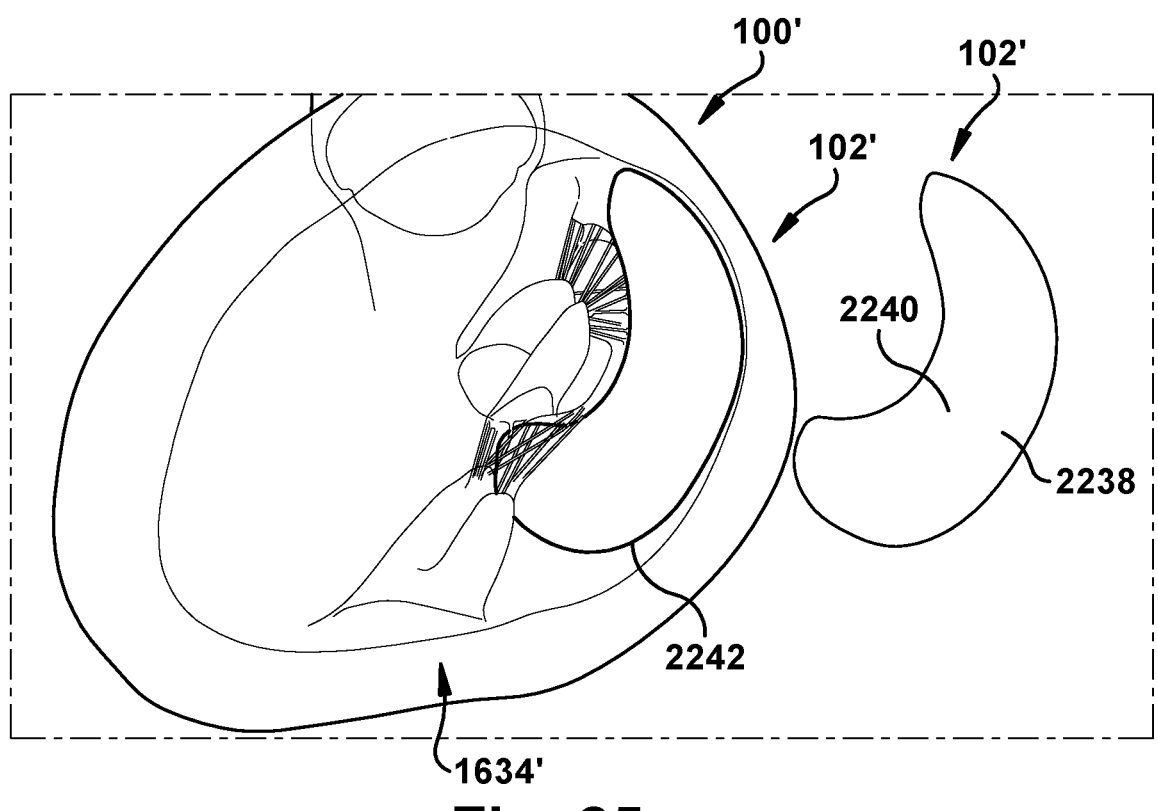
FIG. 25 is a partial bottom perspective view of the aspect of FIG. 22, both inside and outside the example use environment.
Figure 26:
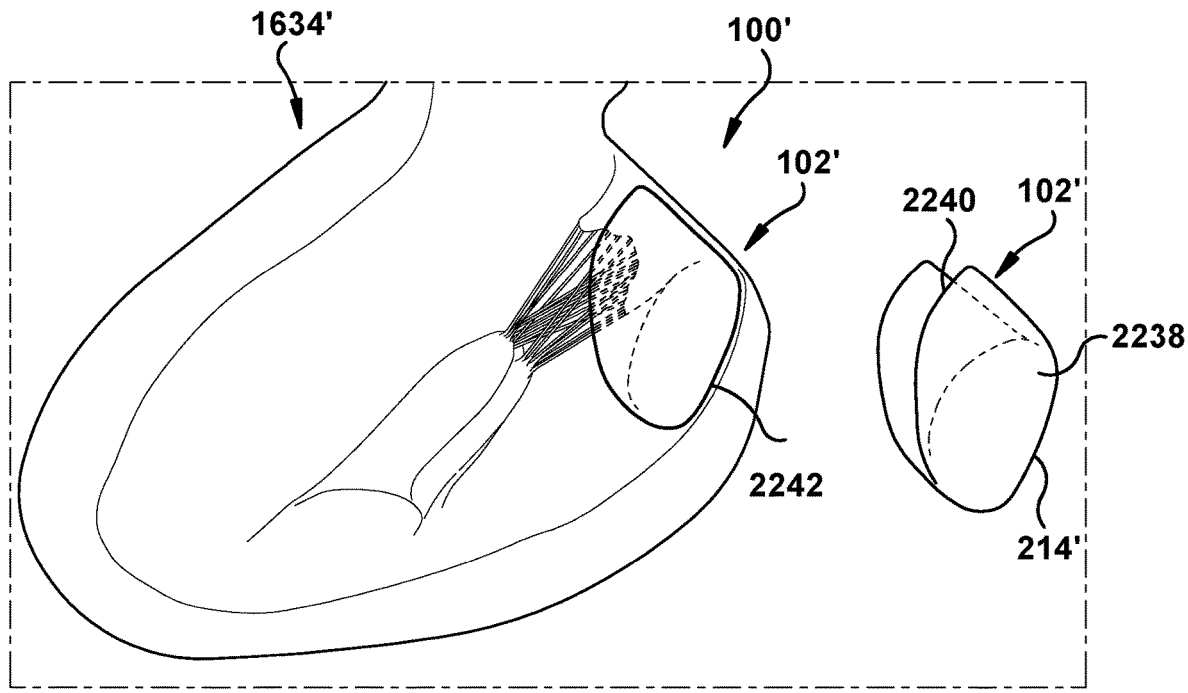
FIG. 26 is a partial side perspective view of the aspect of FIG. 22, both inside and outside the example use environment.
Figure 27:
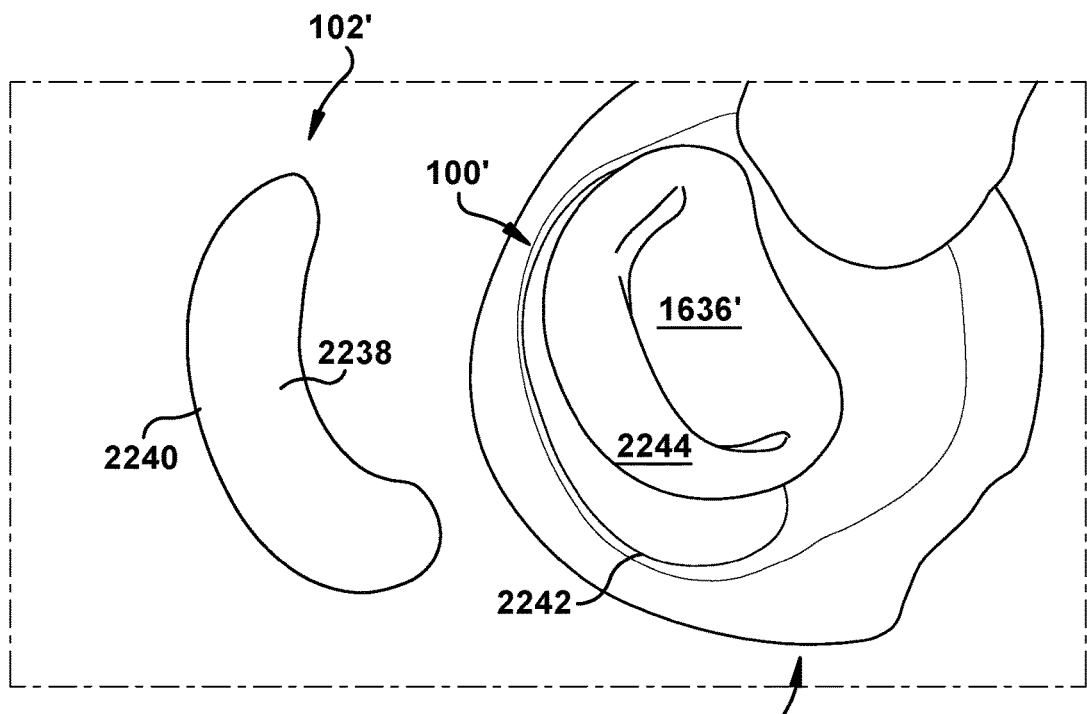
FIG. 27 is a partial top perspective view of the aspect of FIG. 22, both inside and outside the example use environment.
Figure 28:
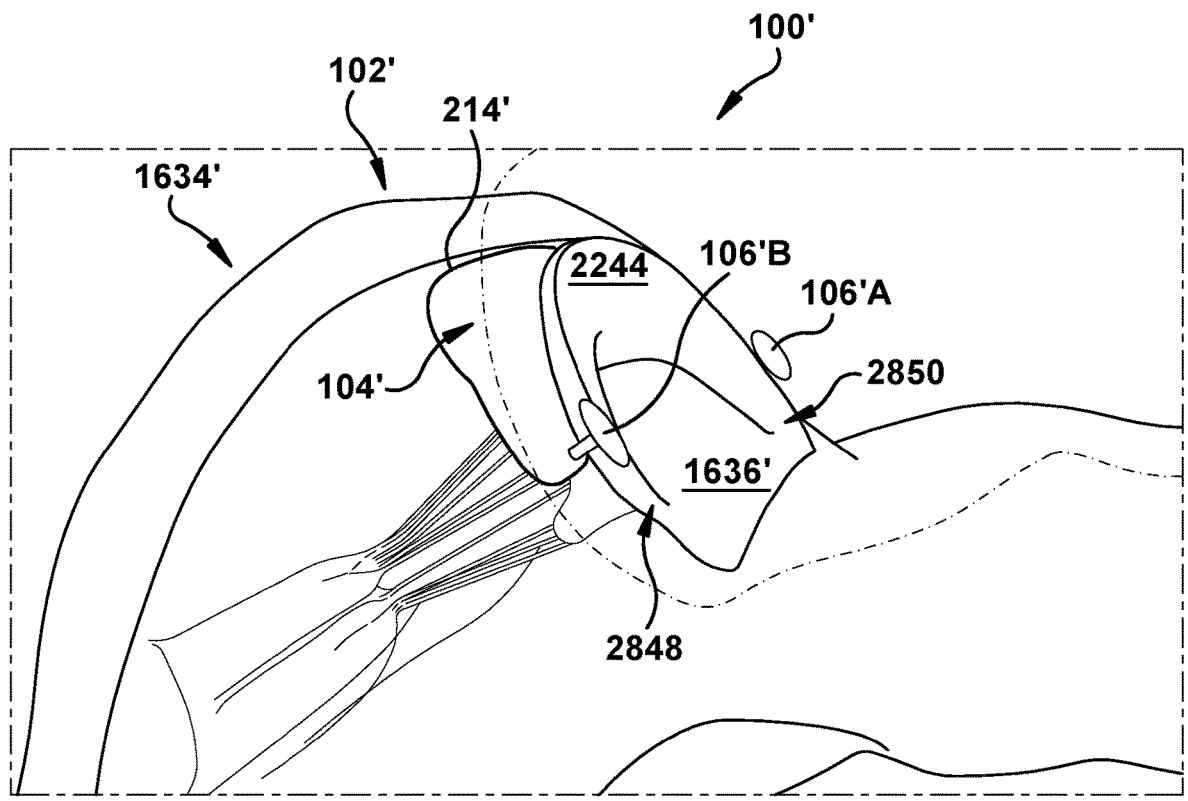
FIG. 28 is a partial side perspective view of an aspect of the invention.
Figure 29:
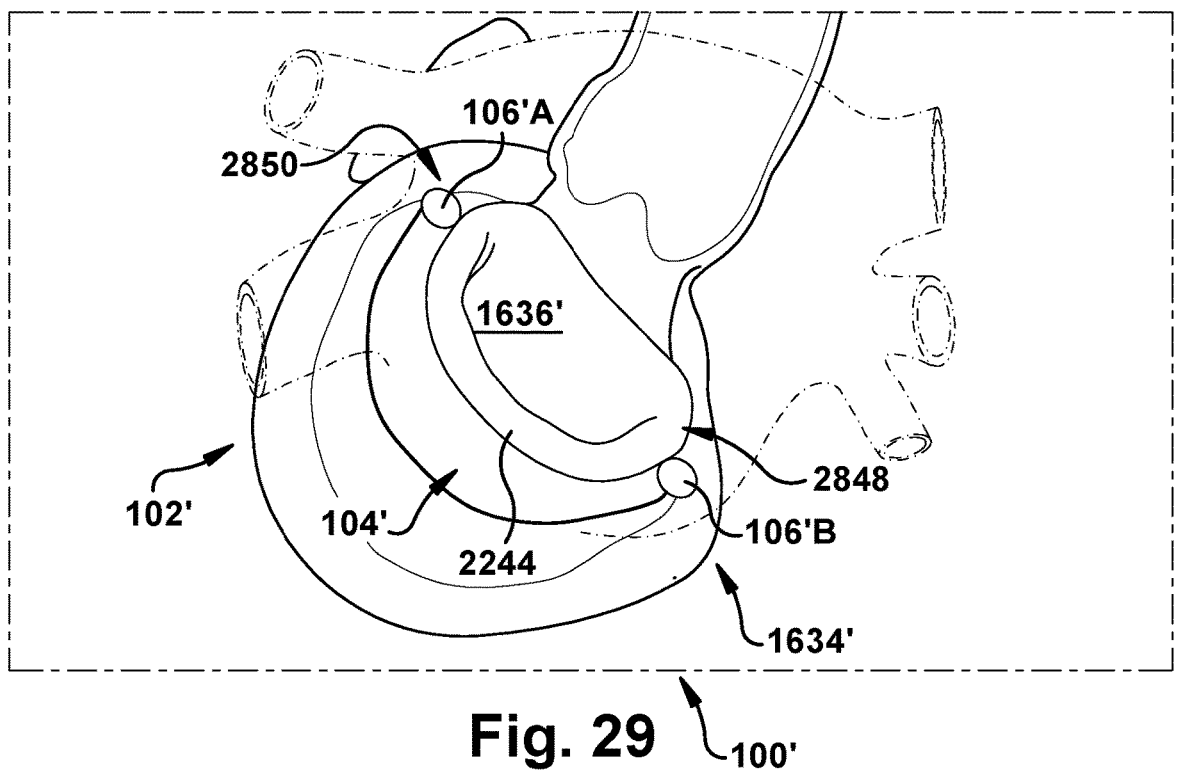
FIG. 29 is a partial top perspective view of the aspect of FIG. 28.
Figure 30:
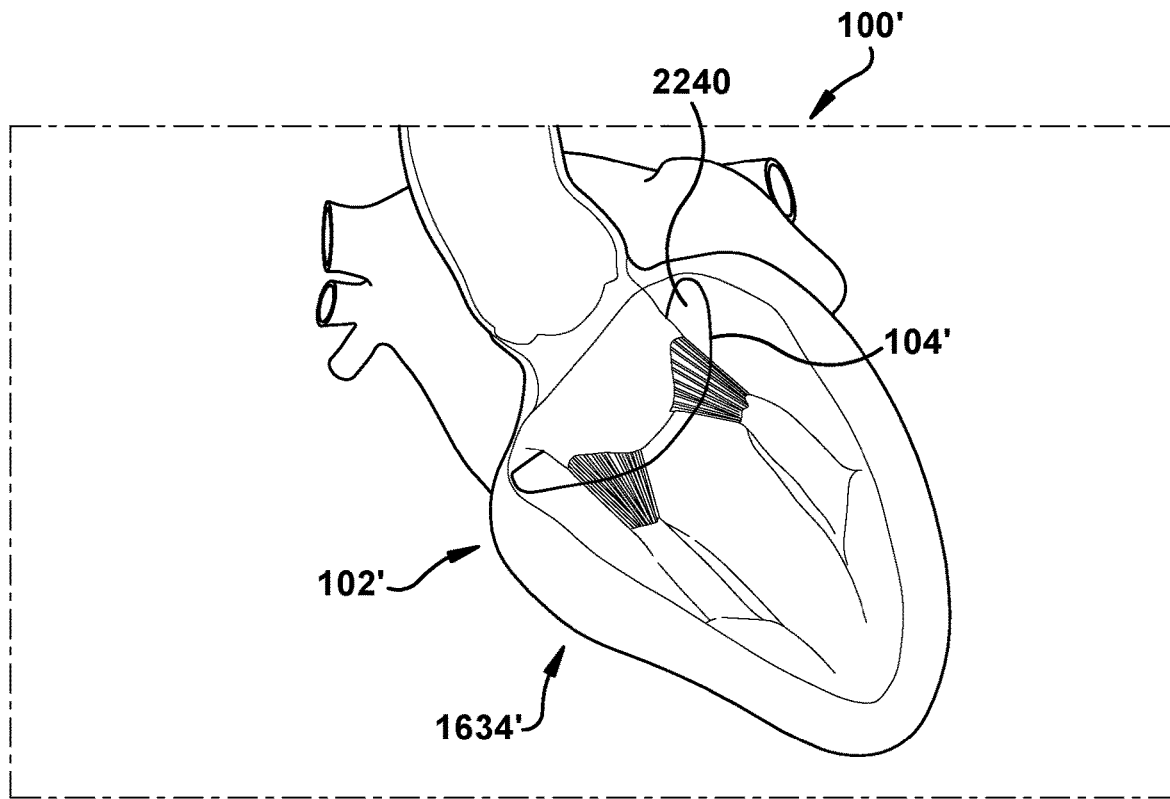
FIG. 30 is a partial side perspective view of the aspect of FIG. 28.

FIG. 15 schematically illustrates a number of different options, which can be used (singly or in combination) for various use environments of the apparatus 100, as desired. The options laid out in FIG. 15 are not exhaustive or exclusive, and an apparatus 100 according to the present invention could include any number, combination, or arrangement of these options. The devices as shown in FIG. 15, as with any embodiment or component of the apparatus 100 shown and/or described herein, can be introduced and delivered under echocardiographic and/or fluoroscopic guidance through a transcatheter or percutaneous approach with a flexible mechanical adjustment catheter transseptally or transfemorally; by transatrial, transapical, transaortic, transcarotid, and/or transsubclavian artery approaches; by open-heart surgery; by robotically assisted surgery; and/or by minimally invasive surgical procedure through direct visualization.

FIGS. 16-21 show a variety of views of an example apparatus 100 in place within a heart 1634, and particularly in a mitral valve 1636 position of the heart 1634. The apparatus 100 of FIGS. 16-21 includes a plurality of subvalvular devices 102. In one of the subvalvular devices 102A of FIGS. 16-21, both the subvalvular supporting portion 104 and the anchor portion 106 are substantially formed of braided mesh strands. In the other of the subvalvular devices 102B of FIGS. 16-21, one of the subvalvular supporting portion 104 and the anchor portion 106 (here, the subvalvular supporting portion 104) is substantially formed of braided mesh strands and the other of the subvalvular supporting portion 104 and the anchor portion 106 (here, the anchor portion 106) is a balloon. The subvalvular supporting portions 104 of both of the subvalvular devices 102 A and 102B of FIGS. 16-21 are of the "elliptical cylinder" configuration previously mentioned. Any number and type(s) of subvalvular devices 102, having any desired physical properties or combinations thereof, could be provided in a single apparatus 100—of any embodiment of the present invention—as desired to reinforce, support, or "bolster" the valve leaflet, and thus achieve desired regurgitation reduction for all the heart valve.

FIGS. 22-31 illustrate a second embodiment of an apparatus 100'. The apparatus 100' of FIGS. 22-31 is similar to the apparatus 100 of FIGS. 1-21 and therefore, structures of FIGS. 22-31 that are the same as or similar to those described with reference to FIGS. 1-21 have the same reference numbers with the addition of a "prime" mark. Description of common elements and operation similar to those in the previously described first embodiment will not be repeated with respect to the second embodiment.

FIGS. 22-31 illustrate an apparatus 100' which includes at least one subvalvular device 102' having a subvalvular supporting portion 104' with a leaflet-contacting upper supporter surface 210' longitudinally spaced from an oppositely facing lower supporter surface 212'. (In FIGS. 22-31, the subvalvular device 102' is shown twice in each picture in substantially the same orientation, once on its own and once in situ in a heart 1634', to better show the shapes and contours being described.) At least one of the upper and lower supporter surfaces 210' and 212' includes a convex outer edge 2238 and a concave inner edge 2240, though once again, it is contemplated that these surfaces may not be strictly delineated from one another because of the rounded contours of the subvalvular supporting portion 104' shown and provided for particular use environments.

A supporter perimeter wall 214' extends longitudinally between, and is integrally and contiguously formed with both of, the upper and lower supporter surfaces 210' and 212'. At least a portion of the supporter perimeter wall 214' contacts a subvalvular cardiac wall 2242 adjacent to the mitral heart valve 1636' concurrently with the concave inner edge 2240 coextending with a posterior leaflet 2244. That is, the concave inner edge 2240 has the same length and contour as a supermajority of, if not substantially an entirety of, the posterior leaflet 2244.

An anchoring feature (shown schematically at 2246) permanently attaches the subvalvular supporting portion 104' to cardiac tissue such that the subvalvular supporting portion 104' substantially prevents movement of the posterior leaflet 2244 during heart function. For example, and particularly when the second embodiment of the apparatus 100 includes a subvalvular supporting portion 104' which is a single-piece balloon as shown in FIGS. 22-27, the anchoring feature 2246 may include at least one of adhesive, tissue ingrowth facilitators, sutures (represented by the "x" marks in FIG. 22), staples, and frictional fit (i.e., a dimensional mismatch such that the heart tissue exerts a compressive force sufficient to resist motion of the subvalvular supporting portion 104').

With reference now to the configuration of the second embodiment of the apparatus 100' shown in FIGS. 28-31, the anchoring feature 2246 includes an anchor portion 106' and a connector neck 108' similar to those discussed above with respect to the first embodiment of the apparatus 100. In fact, as shown in FIGS. 28-31, the anchor portion 106' is a first anchor portion 106'A, and the subvalvular device 102' includes at least one additional anchor portion (here, second anchor portion 106'B) spaced radially from the first anchor portion 106'A. Here, both the subvalvular supporting portion 104' and at least one of the anchor portions 106' are balloons, which can be placed and inflated in any desired manner.

At least a chosen one of the anchor portions 106' may be located at an anterior commissure 2848 of the mitral valve 1636 and at least an other one of the anchor portions 106' may be located at a posterior commissure 2850 of the mitral valve 1636. For example, and shown in FIGS. 28-31, the first anchor portion 106'A is located at the posterior commissure 2850 and the second anchor portion 106'B is located at the anterior commissure 2848. Accordingly, the subvalvular device 102' of FIGS. 20-31 may extend continuously underneath the mitral valve 1636 annulus between the anterior commissure 2848 of the mitral valve 1636 and the posterior commissure 2850 of the mitral valve 1636.

At least one of the first and second anchor portions 106'A and 106'B may be substantially formed of braided mesh strands. At least one of the first and second anchor portions 106'A and 106'B may be a balloon. One of the first and second anchor portions 106'A and 106'B may be substantially formed of braided mesh strands and the other of the first and second anchor portions 106'A and 106'B may be a balloon.

Figure 31:
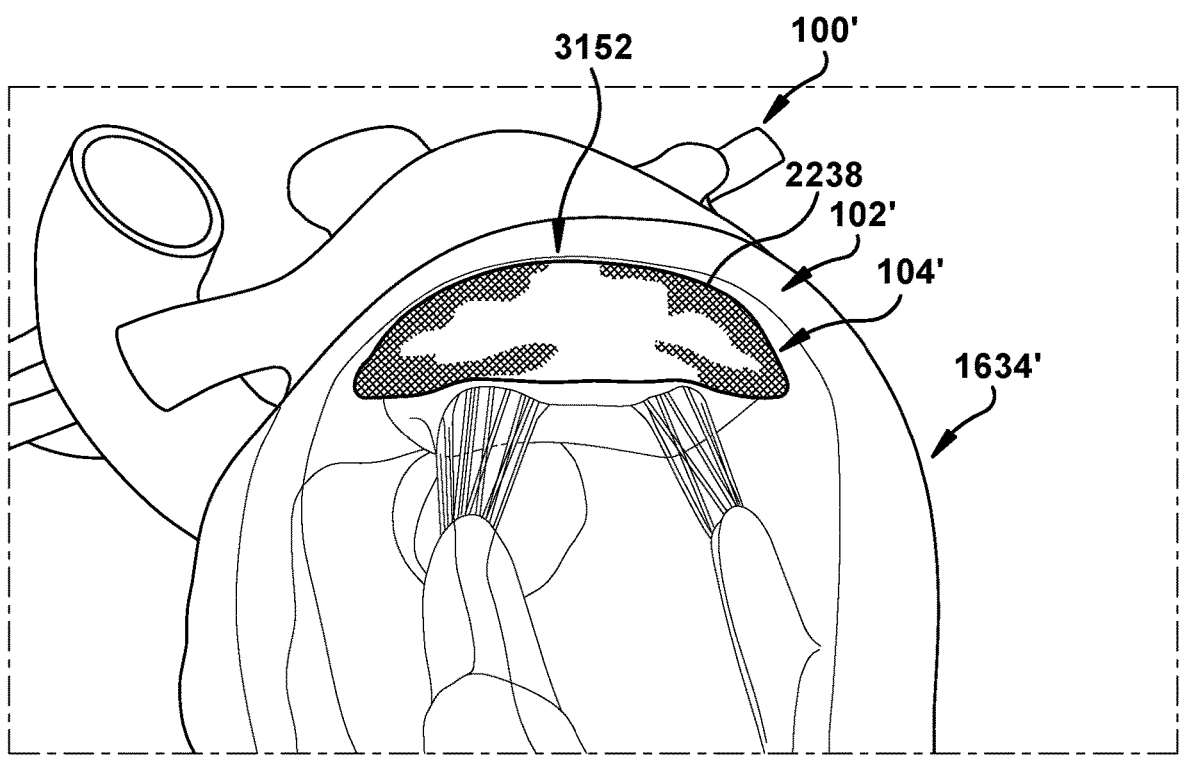
FIG. 31 is a partially bottom perspective view of the aspect of FIG. 28.
Figure 32:
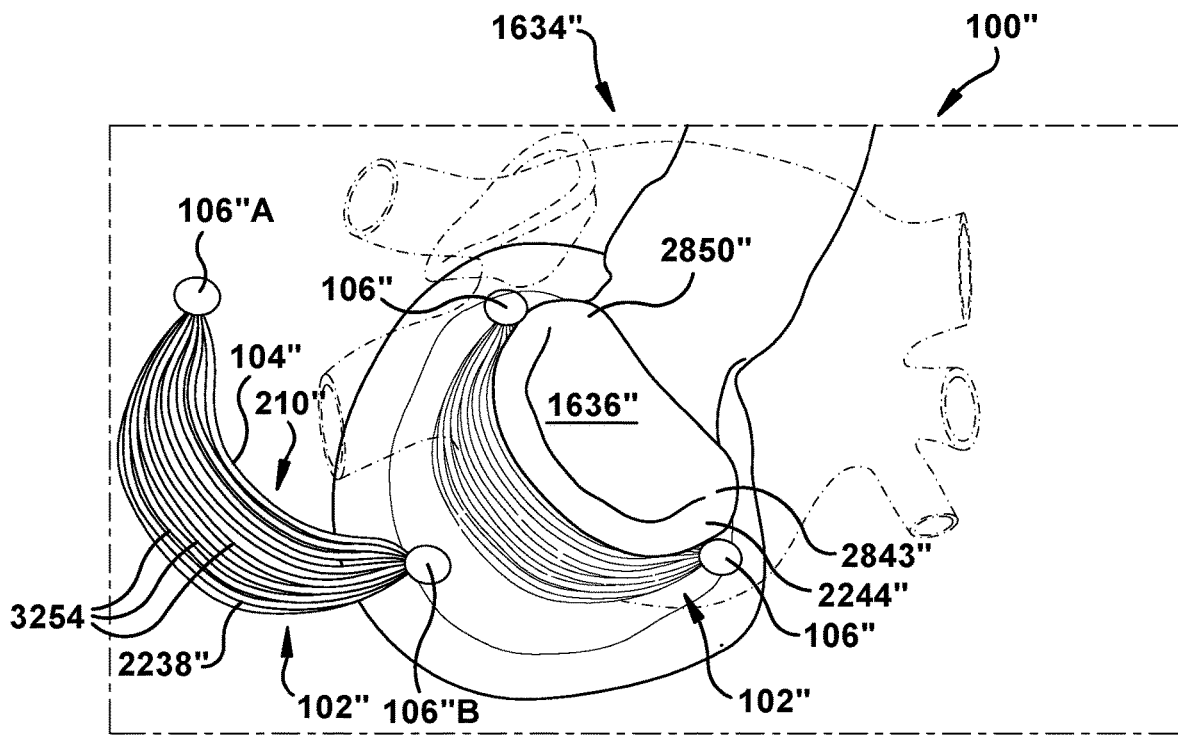
FIG. 32 is a partial top perspective view of an aspect of the invention, both inside and outside an example use environment.
Figure 33:
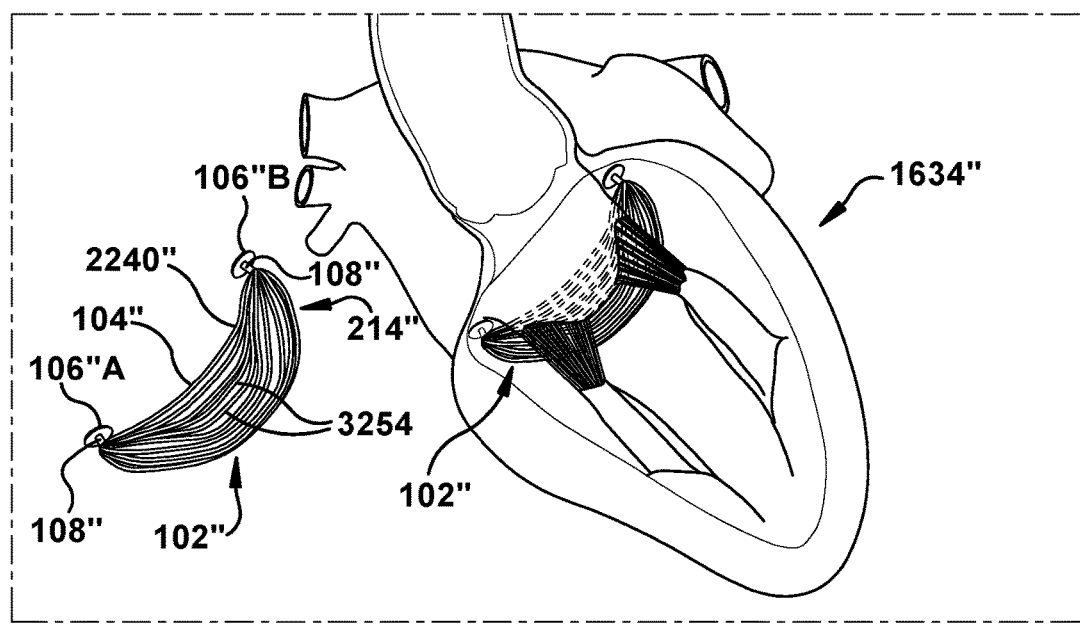
FIG. 33 is a partial bottom perspective view of the aspect of FIG. 32, both inside and outside the example use environment.
Figure 34:
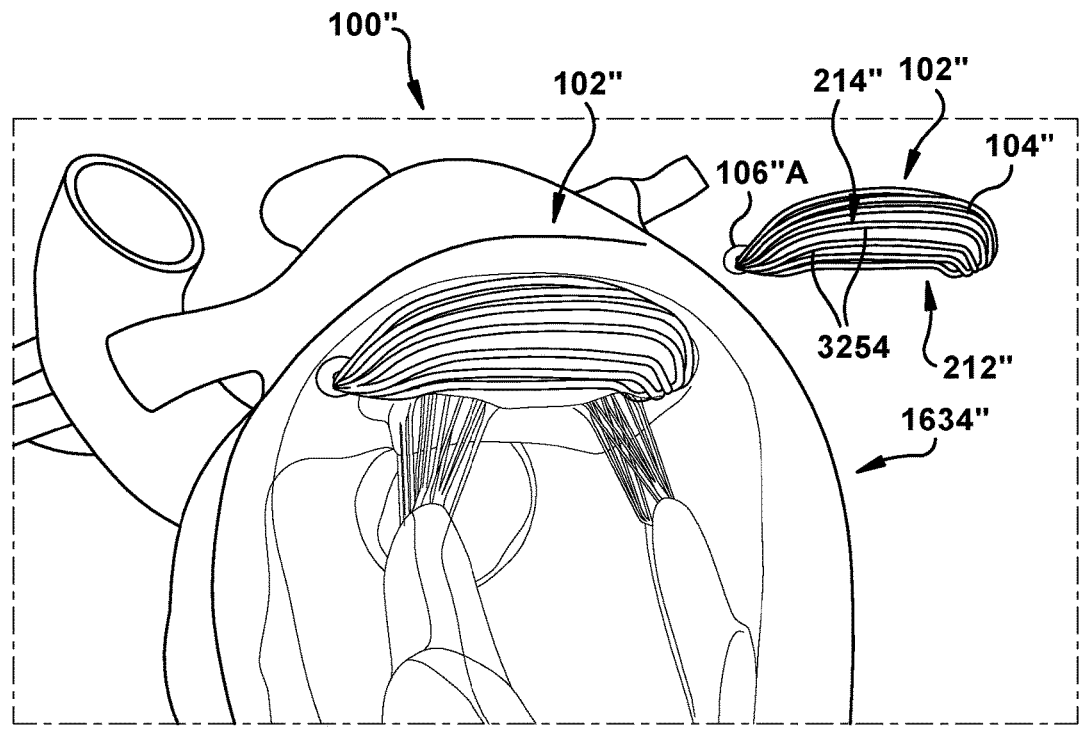
FIG. 34 is a partial side perspective view of the aspect of FIG. 32, both inside and outside the example use environment.
Figure 35:
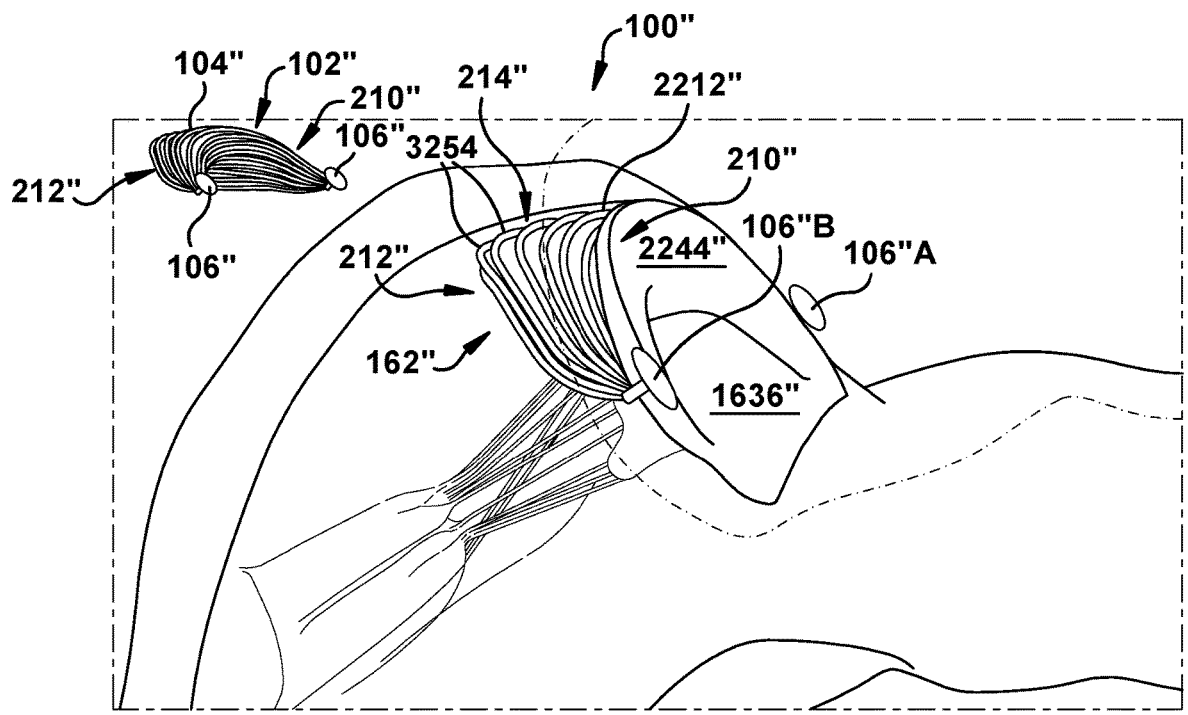
FIG. 35 is a partial side perspective view of the aspect of FIG. 32, both inside and outside the example use environment.

With specific reference to FIG. 31, at least one of the subvalvular supporting portion 104' and the anchor portion 106' is a balloon, as shown here. The subvalvular device 102' shown as an example in FIG. 31 includes a separately provided covering material (shown schematically at 3152 as a mesh material) attached to a majority of an outer surface of the subvalvular device 102'. This covering material 3152 could be of any type and could be provided for any desired reason such as, but not limited to, promotion or inhibition of tissue ingrowth and/or prevention of rejection of the apparatus 100' by the body.

FIGS. 32-35 illustrate a third embodiment of a device 100". The device 100" of FIGS. 32-35 is similar to the devices 100, 100' of FIGS. 1-31 and therefore, structures of FIGS. 32-35 that are the same as or similar to those described with reference to FIGS. 1-31 have the same reference numbers with the addition of a double "prime" mark. Description of common elements and operation similar to those in the previously described first and second embodiments will not be repeated with respect to the third embodiment.

FIGS. 32-35 illustrate an apparatus 100" which includes at least one subvalvular device 102" having a subvalvular supporting portion 104" with a leaflet-contacting upper supporter surface 210" longitudinally spaced from an oppositely facing lower supporter surface 212". (In FIGS. 32-35, the subvalvular device 102" is shown twice in each picture in substantially the same orientation, once on its own and once in situ in a heart 1634", to better show the shapes and contours being described.) At least one of the upper and lower supporter surfaces 210" and 212" includes a convex outer edge 2238" and a concave inner edge 2240", though once again, it is contemplated that these surfaces may not be strictly delineated from one another because of the rounded contours of the subvalvular supporting portion 104" shown and provided for particular use environments.

At least a portion of each of the upper and lower supporter surfaces 210" and 212" and the supporter perimeter wall 214" are formed from a plurality of radially extending struts 3254 which extend substantially parallel to each other along at least a portion of the length thereof. At least a portion of the supporter perimeter wall 214" contacts a subvalvular cardiac wall 2242" adjacent to the mitral heart valve 1636" concurrently with the concave inner edge 2240" coextending with a posterior leaflet.

Similarly to the second embodiment of the apparatus 100' shown in FIGS. 28-31, the third embodiment of the apparatus 100" shown in FIGS. 32-35 includes a first anchor portion 106"A located at the posterior commissure 2850 and a second anchor portion 106"B is located at the anterior commissure 2848. Accordingly, the subvalvular device 102" of FIGS. 32-35 extends continuously underneath the mitral valve 1636" annulus between the anterior commissure 2848" of the mitral valve 1636" and the posterior commissure 2850" of the mitral valve 1636".

At least one of the first and second anchor portions 106"A and 106"B may be substantially formed of braided mesh strands. At least one of the first and second anchor portions 106"A and 106"B may be a balloon. One of the first and second anchor portions 106"A and 106"B may be substantially formed of braided mesh strands and the other of the first and second anchor portions 106"A and 106"B may be a balloon.

The subvalvular supporting portion 104" may include a separately provided covering material attached to a majority of an outer surface thereof, for any desired reason.

With reference now to FIGS. 36-48, a method for at least partially supporting or untethering a leaflet of a regurgitant heart valve using an apparatus 100 according to any aspect or embodiment of the present invention will be described. One subvalvular device 102, of the type shown in FIGS. 16-21, is shown in FIGS. 36-48 for the sake of discussion. However, it is contemplated that any number or type of subvalvular devices 102 could be used in apparatus 100 via the method described below, such as, but not limited to, any one or more of the structures shown and described in FIGS. 1-35.

Figure 36:
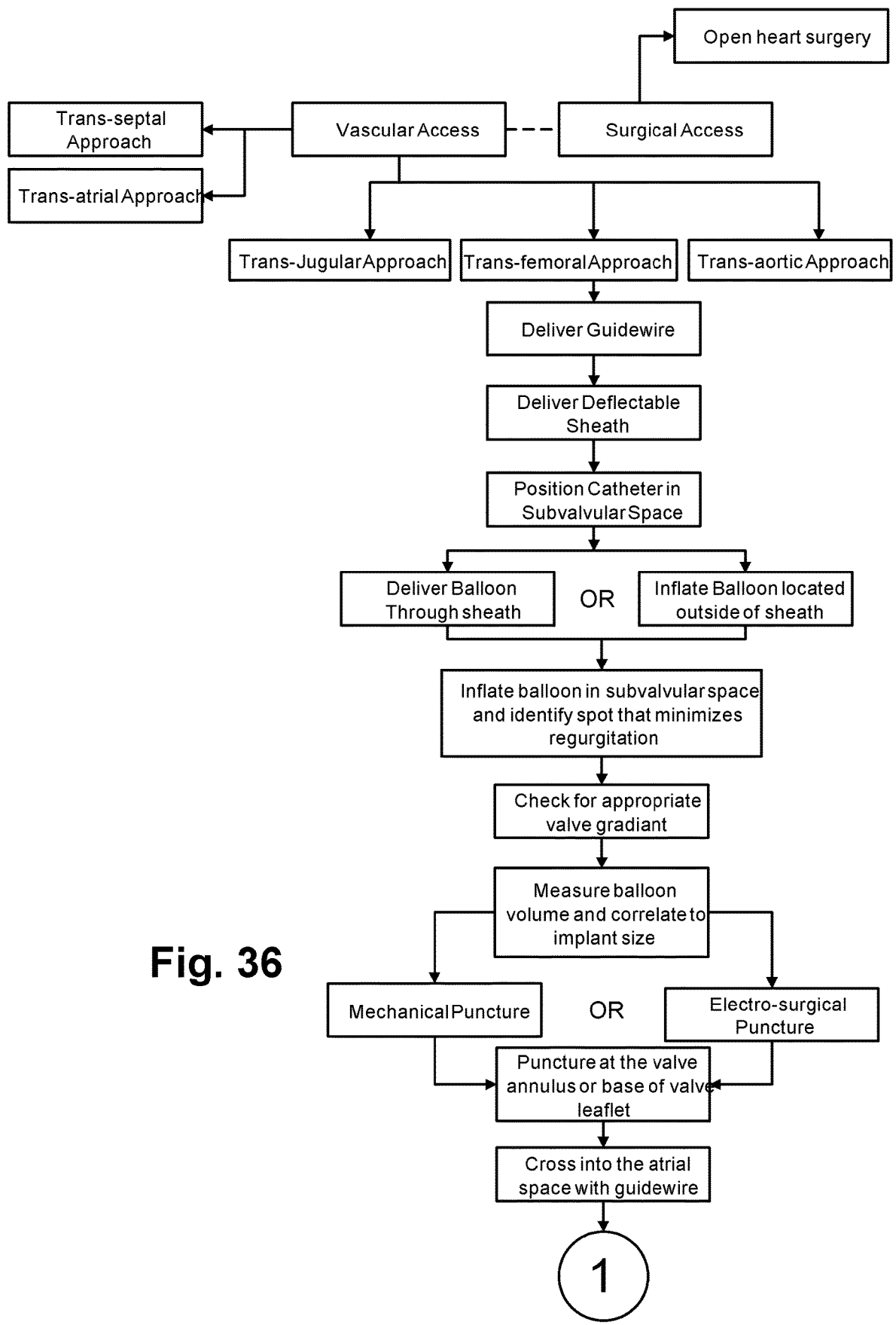
FIGS. 36-37 are a flowchart giving an example use sequence of any aspect of the present invention.
Figure 37:
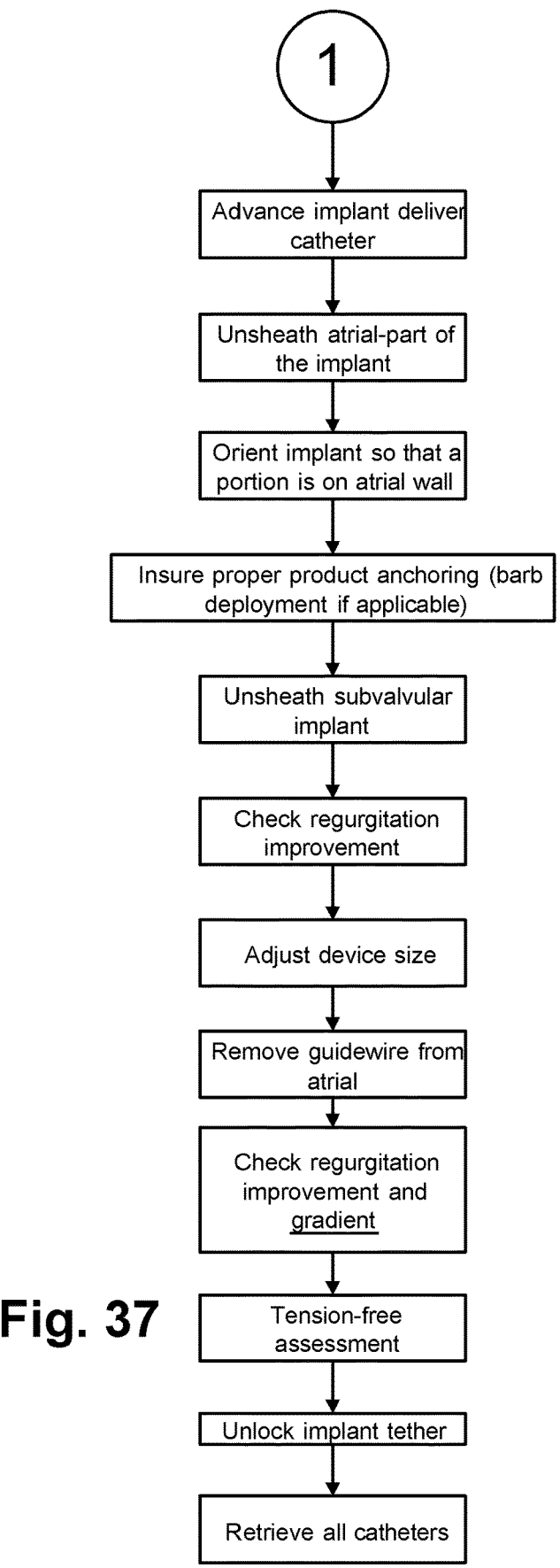

An example flowchart of a method incorporating the below description is shown in FIGS. 36-37, where the circled "1" represents a continuation of the flowchart from FIG. 36 to FIG. 37. The flowchart of FIGS. 36-37 illustrates one potential approach (a transfemoral approach) for providing a patient with an apparatus 100 according to the present invention. FIGS. 38-48, as described below, depict another, potentially related, example approach. One of ordinary skill in the art will be able to provide a suitable surgical approach and corresponding apparatus 100, configured as desired, for a particular use environment without harm to the present invention.

Figure 38:
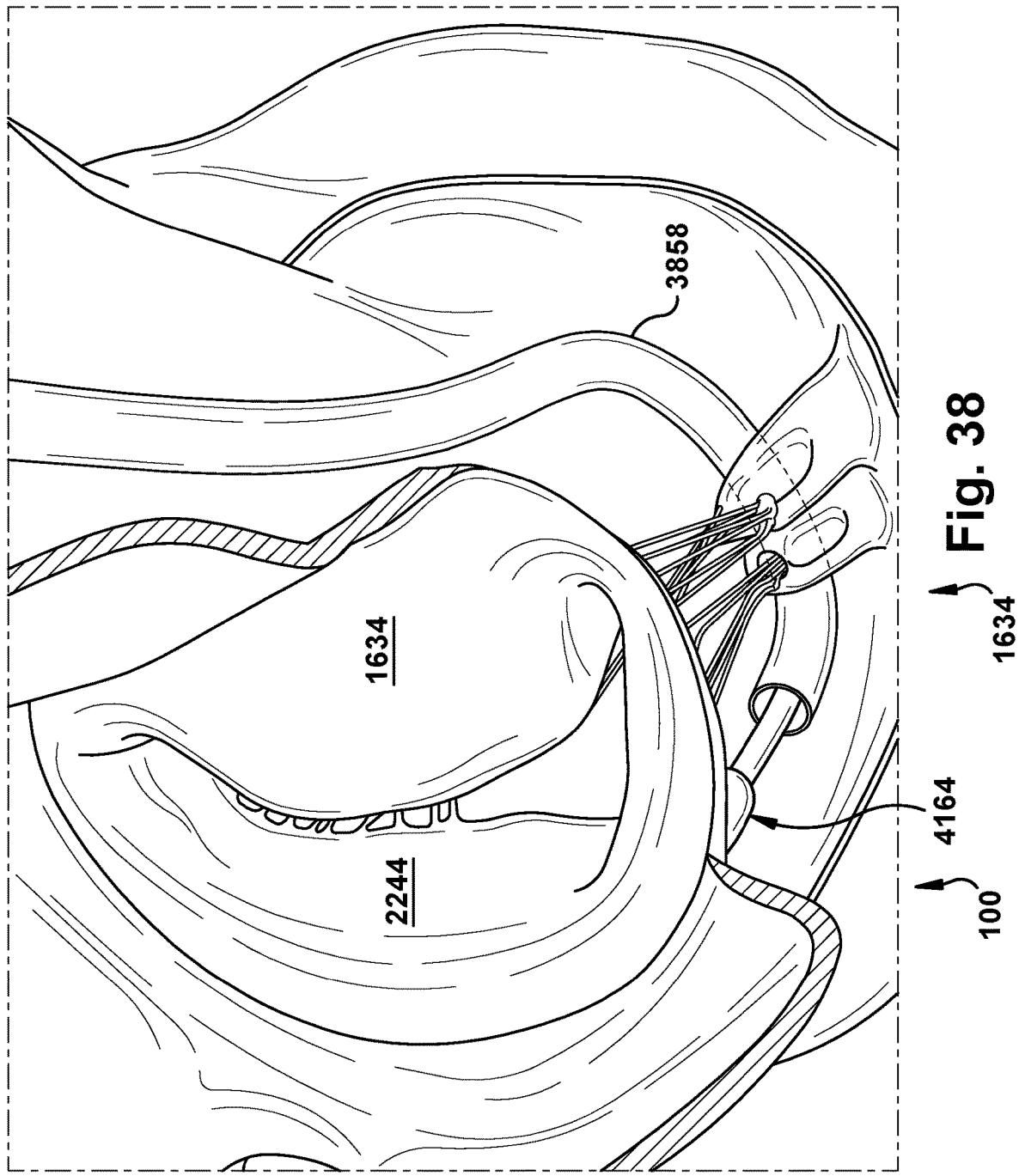
Figure 39:
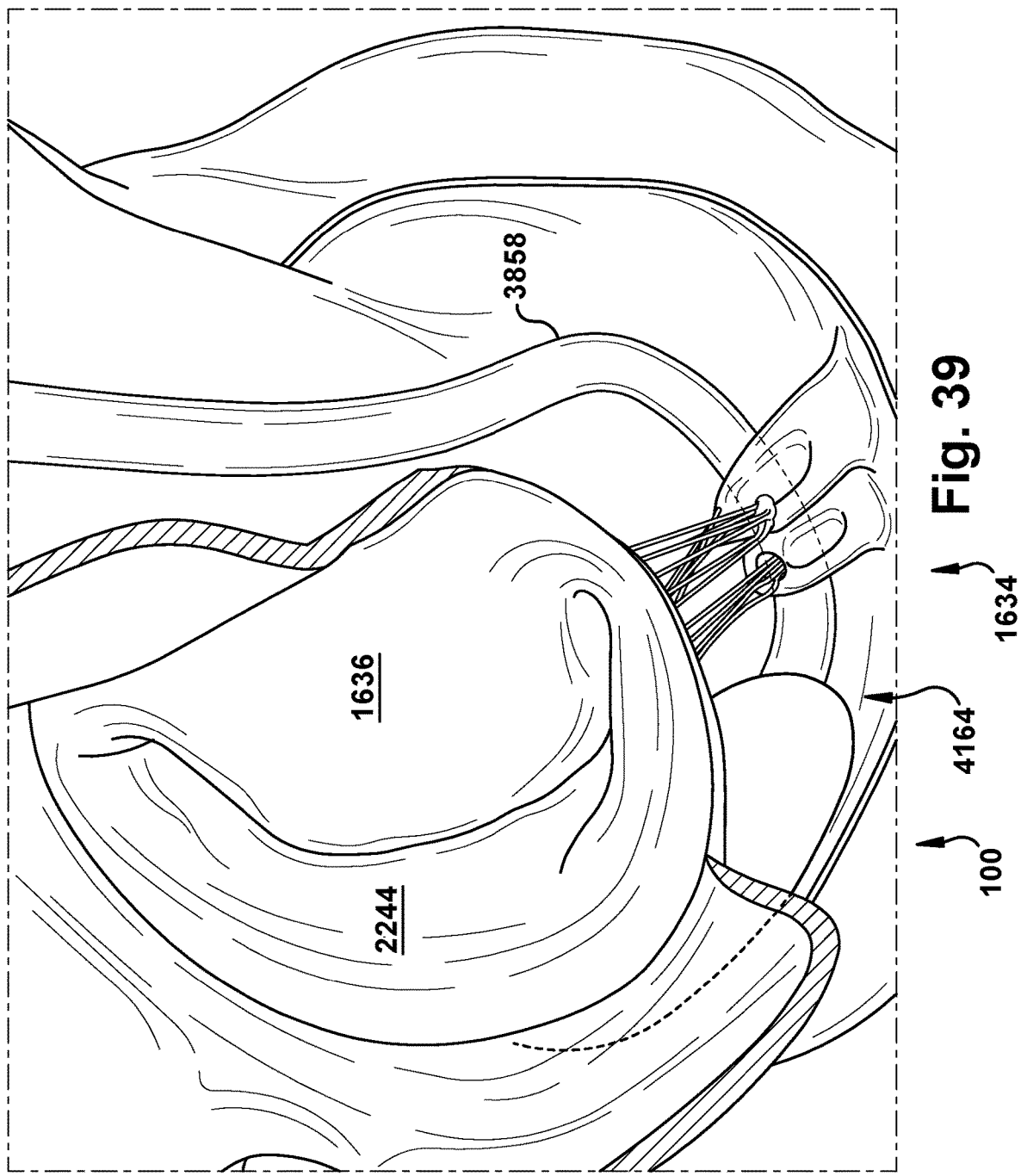
Figure 40:
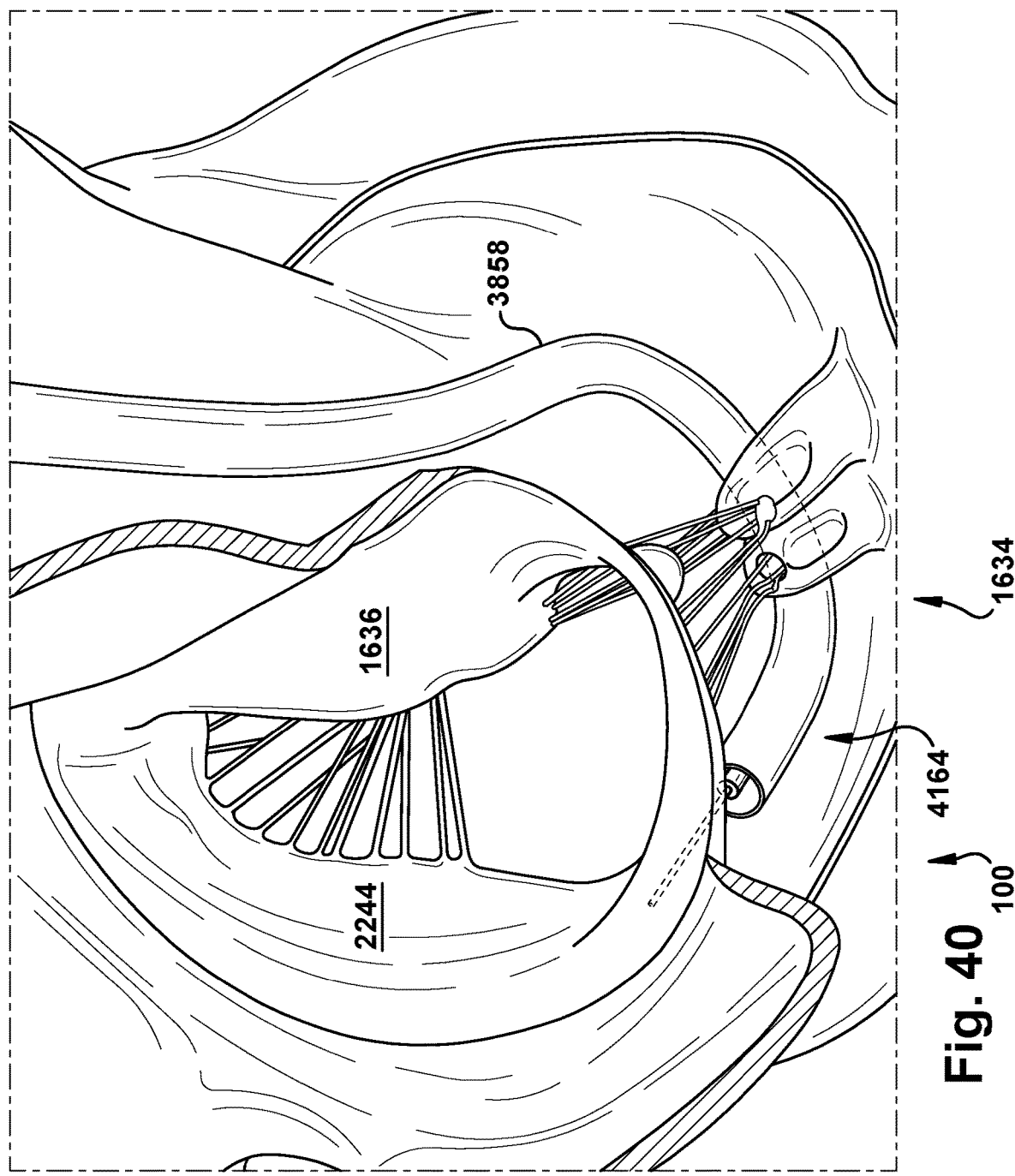

As shown in FIGS. 38-40, a variable-dimension sizer 4164 may be placed adjacent the manufactured puncture site 4060 at a location on a lower side of the leaflet 2244. The sizer 4164 could be, for example, a balloon, as shown, with a shape mimicking that of the subvalvular supporting portion 104 of a corresponding subvalvular device 102 to be implanted in the heart 1634. At least one dimension of the sizer 4164 could be varied, as shown in FIG. 39, to ascertain the presence of a predetermined effect upon the leaflet 2240 responsive to the at least one sizer 4164 dimension. As shown in FIG. 40, then, the sizer 4164 could be deflated and retracted from the heart 1634.

Stated in more detail, when used, the sizer 4164 can be delivered in a retrograde fashion through a transfemoral, transbrachial, or transradial access, or in any other desired manner, for both subvalvular mitral spacer device implantation approaches. The sizer 4164 can go through a beating aortic valve and flex toward the ventricular side of mitral valve 1636 annulus, for placement under the mitral valve leaflet 2244 in the ventricular subvalvular space location surrounding by the left ventricular posterior wall. The physician can navigate the sizer 4164 inside the subvalvular space by fluoroscopy and/or TEE guidance, such as via a catheter 3858, until the sizer 4164 reaches the desired location (e.g., P1, P2, and/or P3 leaflet scallop levels) and is oriented at a desired vector pointing the sizer 4164 from the ventricle toward the atrium. The sizer 4164 may be inflated in the preselected anatomical position. Using any desired imaging means, such as, but not limited to, 2D or 3D real time echocardiograph, the physician can assess the reduction or elimination of mitral valve regurgitation by pushing or moving forward the tethering posterior leaflet 2244 by the sizer 4164 expansion. This "test" sizer 4164 inflation can help to show the surface of leaflet 2244 coaptation between the posterior 2244 and the anterior leaflets before the implantation of an at least semi-permanent subvalvular device 102. The size of the sizer 4164 inflation also can be measured by increasing the saline solution volume from small, to medium, to large or even extra-large size, as desired. Thus, the operator can assess and calibrate the final subvalvular device 102 size appropriate to achieve the desirable competent mitral valve 1636 function, as well as the proper positioning for that subvalvular device 102, through the use of the sizer 4164.

A guidewire 3856 may be placed into the patient's heart 1634, at any desired time during the procedure, where it will remain throughout the majority of the method described herein. In the example procedure shown and described herein, the guidewire 3856 is shown as being placed and used as in the sequence of FIGS. 41-43, after the sizer 4164 has been employed. However, it is contemplated that the guidewire 3856 could also or instead be used in conjunction with the sizer 4164, as desired.

Regardless of when in the surgical procedure it is introduced, though, the guidewire may be placed in any suitable manner, such as, but not limited to minimally invasive surgical techniques. A catheter 3858 may be guided into the patient's heart 1634 via the guidewire 3856. The catheter 3858 can then be used to introduce various structures into the heart 1634, for temporary or permanent location they are in conjunction with installation of the apparatus 100. For example, the guidewire 3856 and/or a subvalvular device 102 could be advanced through a catheter 3858 and into the heart 1634.

Figure 41:
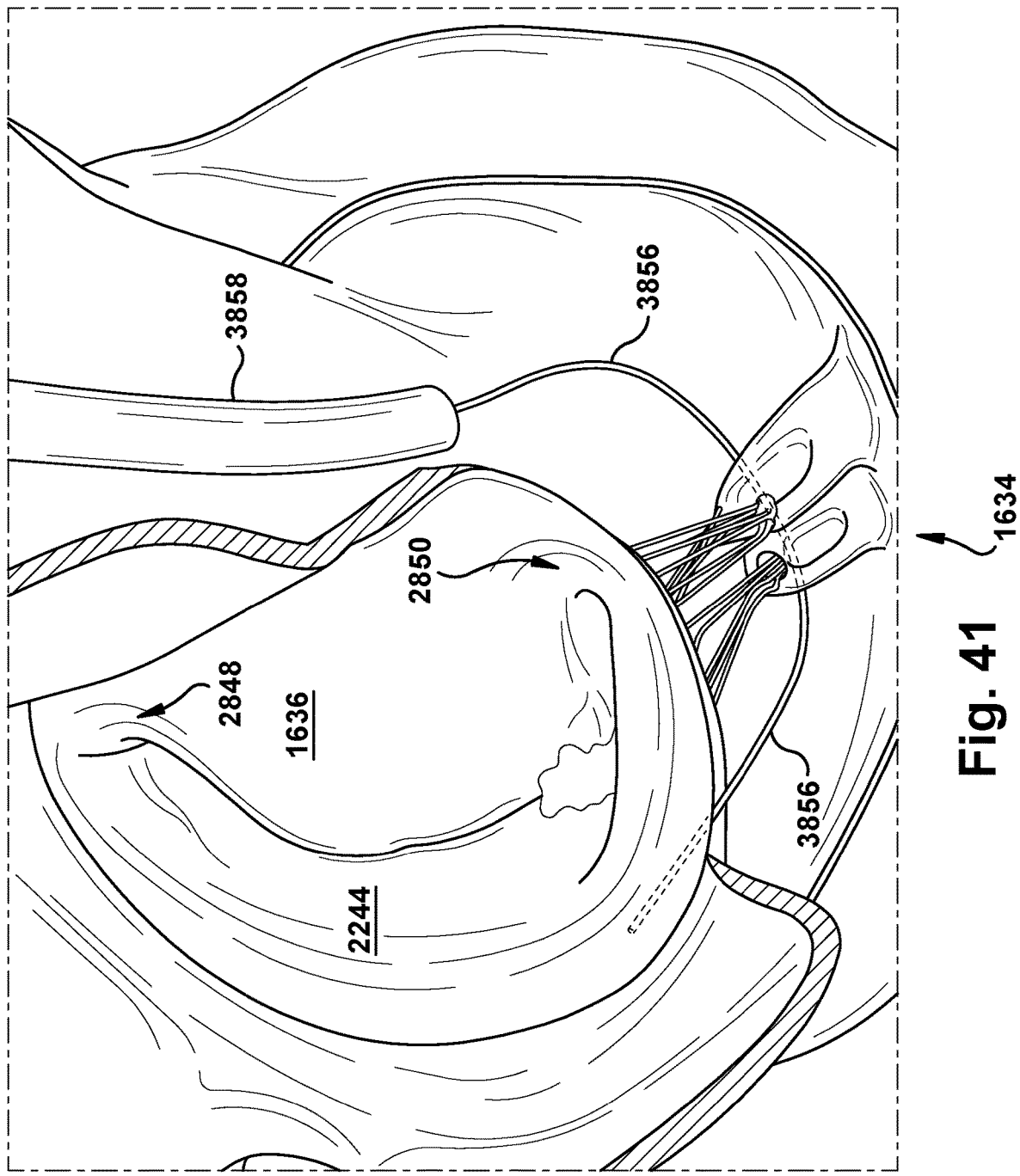
Figure 42:
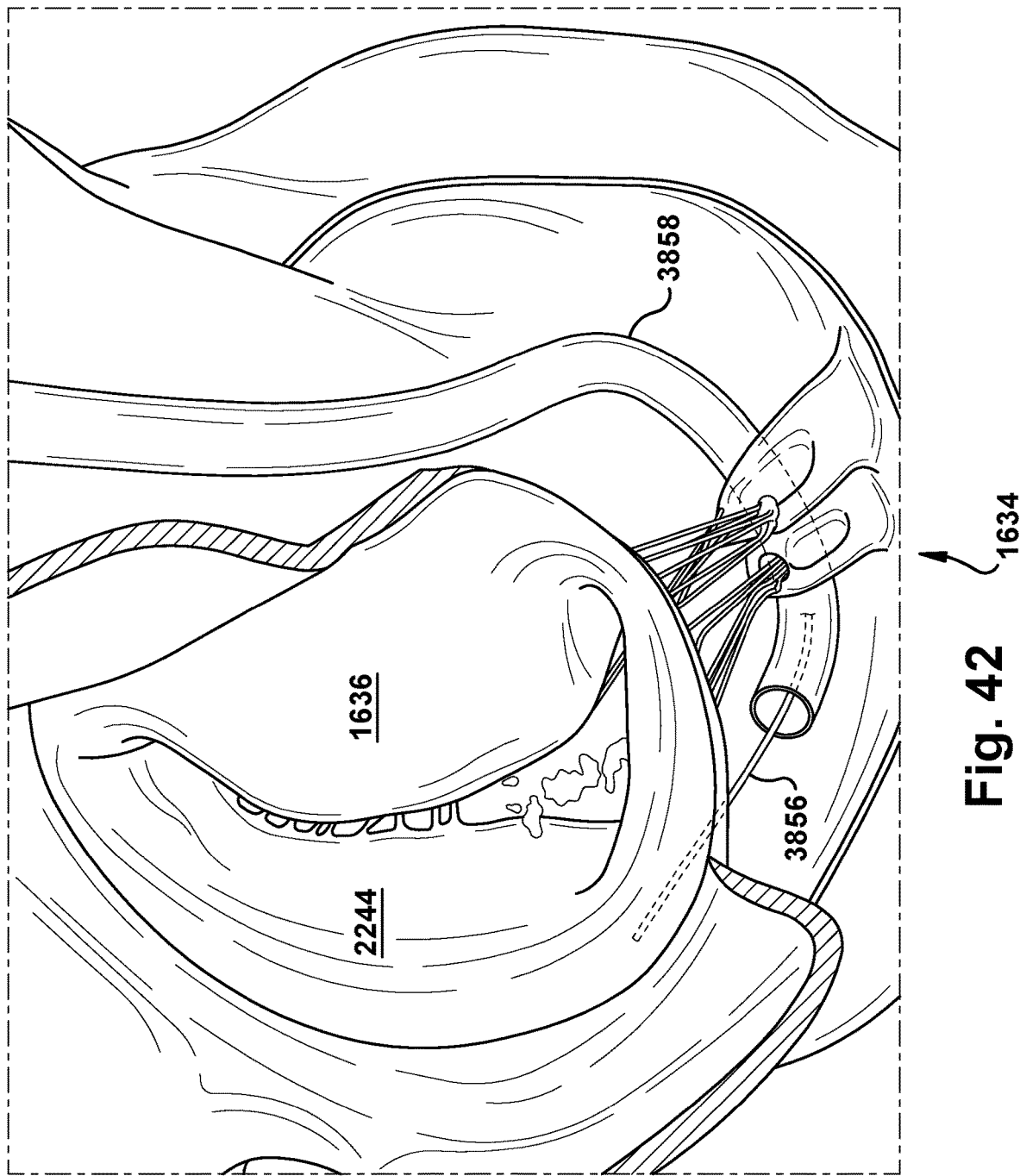
Figure 43:
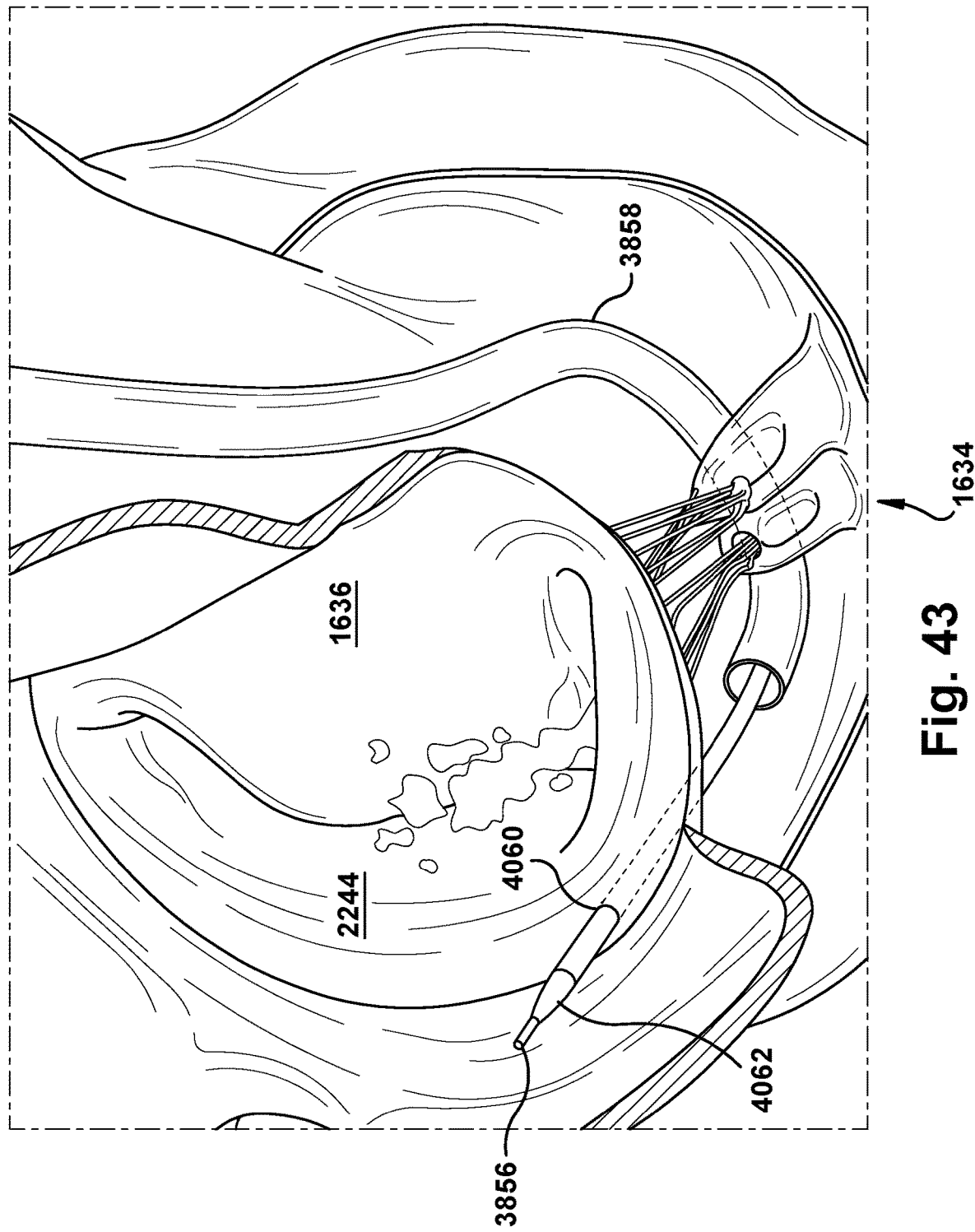

As shown in the sequence from FIGS. 41-43, the guidewire 3856 may be advanced longitudinally through the valve-adjacent heart tissue, shown and described herein as being at least one of a base of a posterior leaflet 2244 and an annulus of the mitral valve 1636. However, it is also contemplated that the apparatus 100 could be installed, using a similar technique, in relationship with a tricuspid and/or aortic valve of a heart 1634.

With specific reference to FIGS. 41-42, the guidewire 3856 and/or any other desired surgical tool, may penetrate completely through at least one of a base of a posterior leaflet 2244 and an annulus of the mitral valve 1636 to create a manufactured puncture site 4060. The guidewire 3856 could be fed through the heart tissue itself, or another surgical tool could be used to help pierce the heart tissue. For example, the manufactured puncture site 4060 could be created by mechanically cutting through the heart tissue with a physically sharp puncture device 4062, like the depicted needle, and/or by electrosurgically cutting through the heart tissue with an electrically-powered cutting device, such as a Bovie knife or cauterizing probe, or application of local RF energy. Once the manufactured puncture site 4060 has been created, the puncture device 4062 or other component/ structure (when present) may then be retracted from the body, such as through the catheter 3858, when present.

Returning to the method as depicted in FIGS. 38-48, then, whether or not a sizer 4164 is used, a subvalvular device 102 is provided, such as any of those depicted and described herein, or any other subvalvular devices 102 configured by one of ordinary skill in the art with reference to the teachings of the present application. Optionally, when a sizer 4164 is used, a particular subvalvular device 102 for implantation could be selected from a plurality of provided subvalvular devices responsive to the varying of the at least one dimension of the sizer 4164. For example, if the user finds that inflation of the sizer 4164 to a "medium" dimension results in a desired reduction in regurgitation of the mitral valve 1636, a "medium" sized subvalvular device 102 could be selected for use with that patient.

Figure 44:
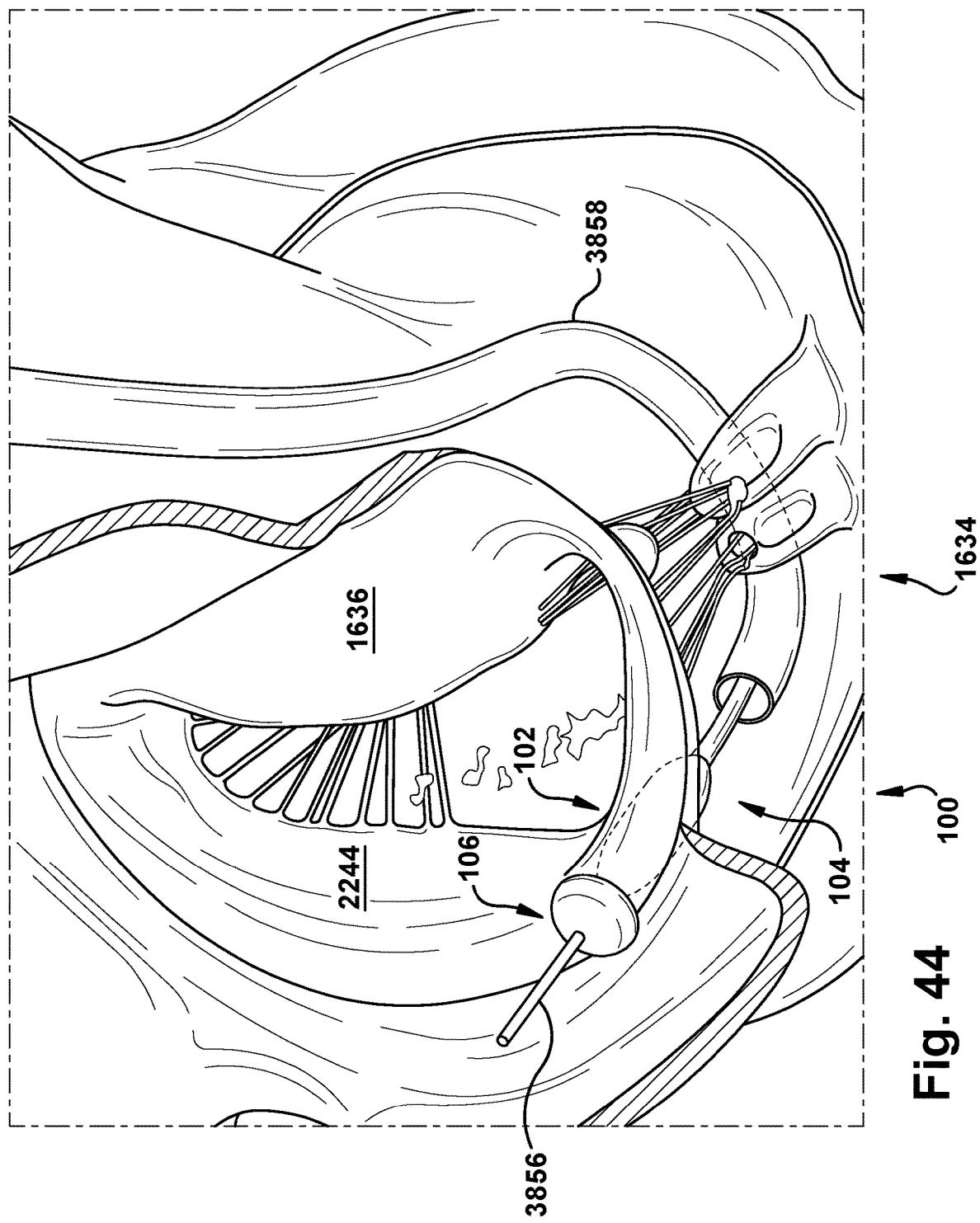
Figure 45:
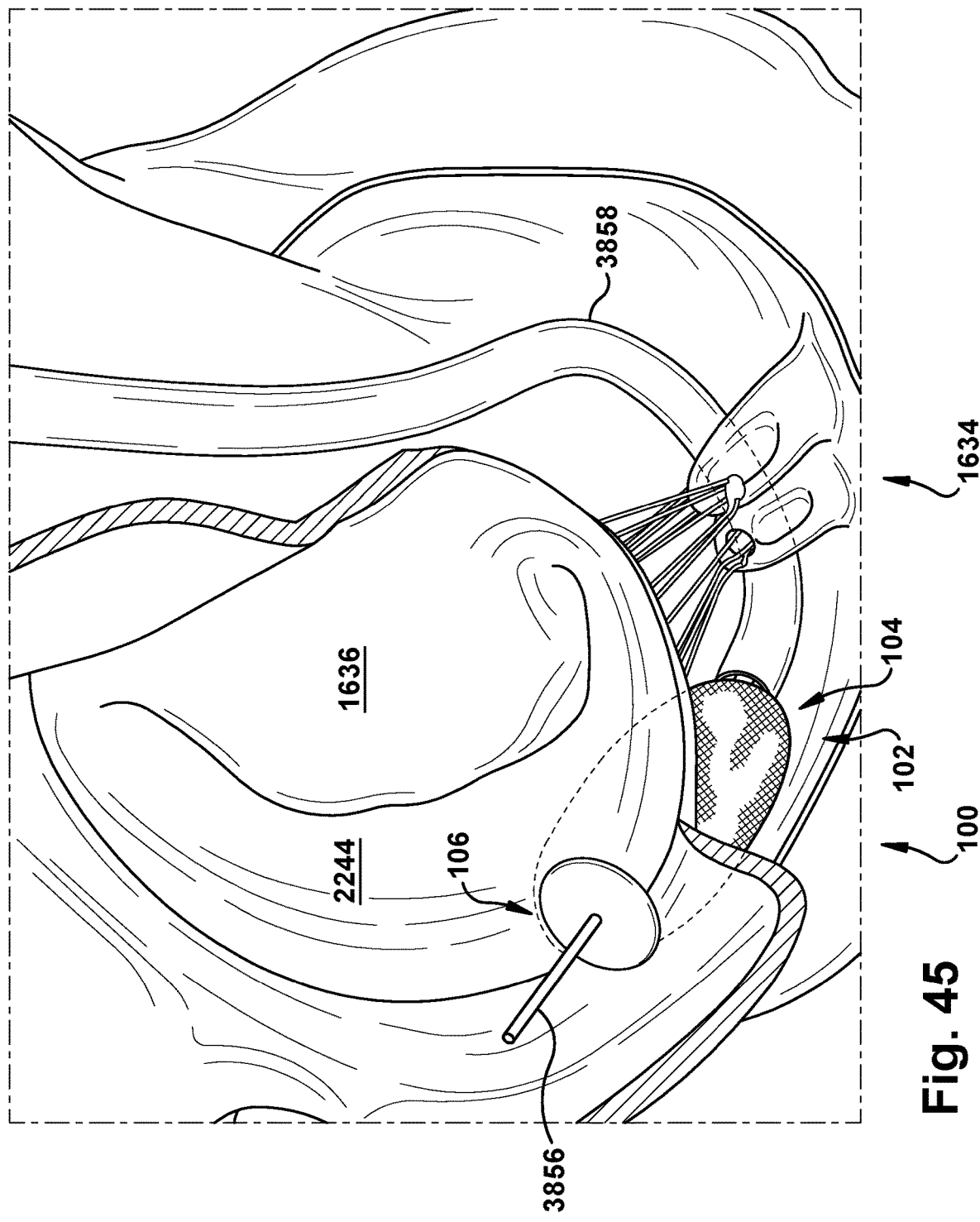

As shown in FIG. 44, the subvalvular device 102 can be advanced into the heart 1634. The anchor portion 106 can be advanced through the manufactured puncture site 4060 to a predetermined anchor location on an upper side of at least one of a base of a posterior leaflet 2244 and an annulus of the mitral valve 1636. The anchor portion 106 can then be deployed at the predetermined anchor location, as shown in FIG. 44.

Figure 46:
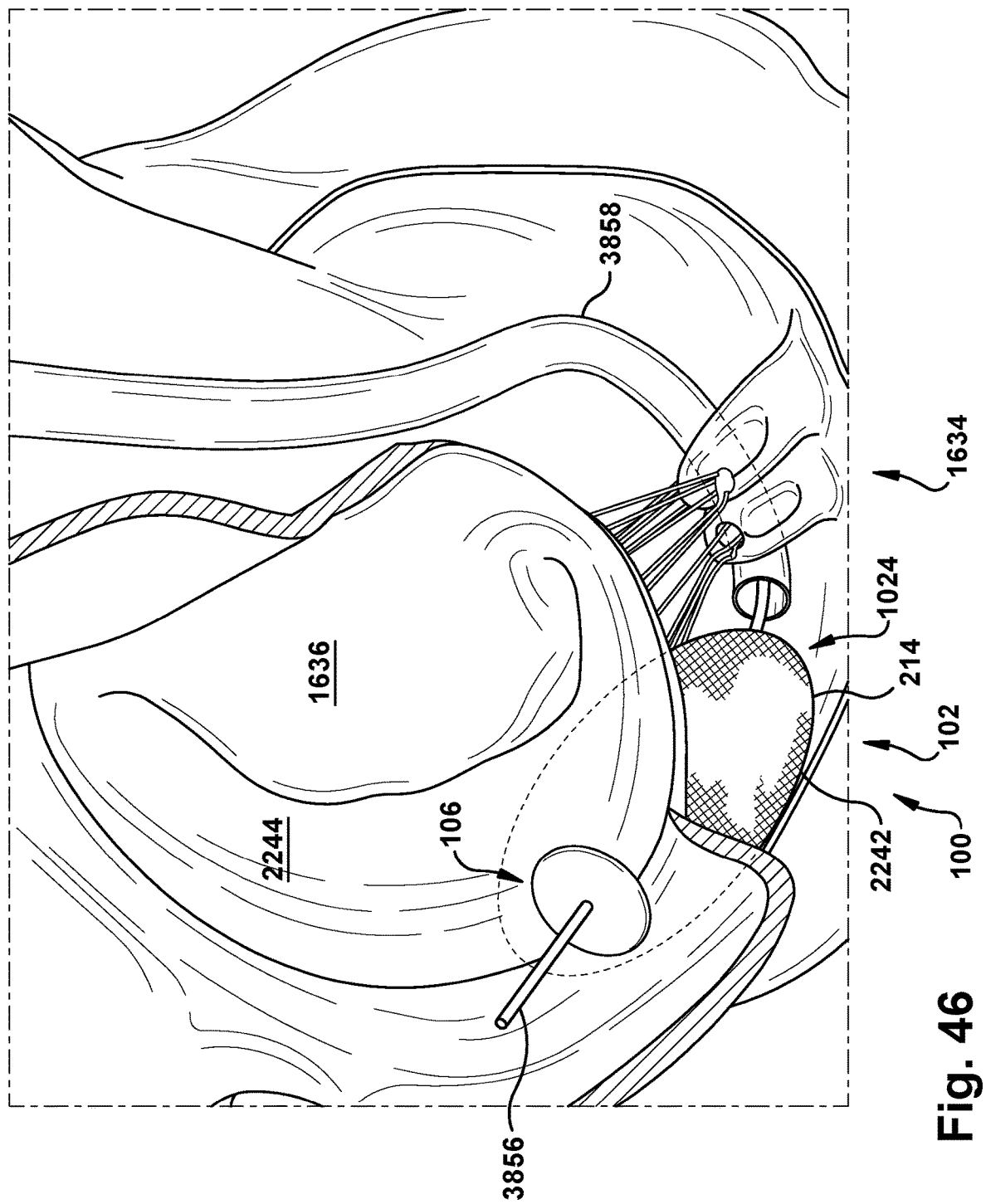
Figure 47:
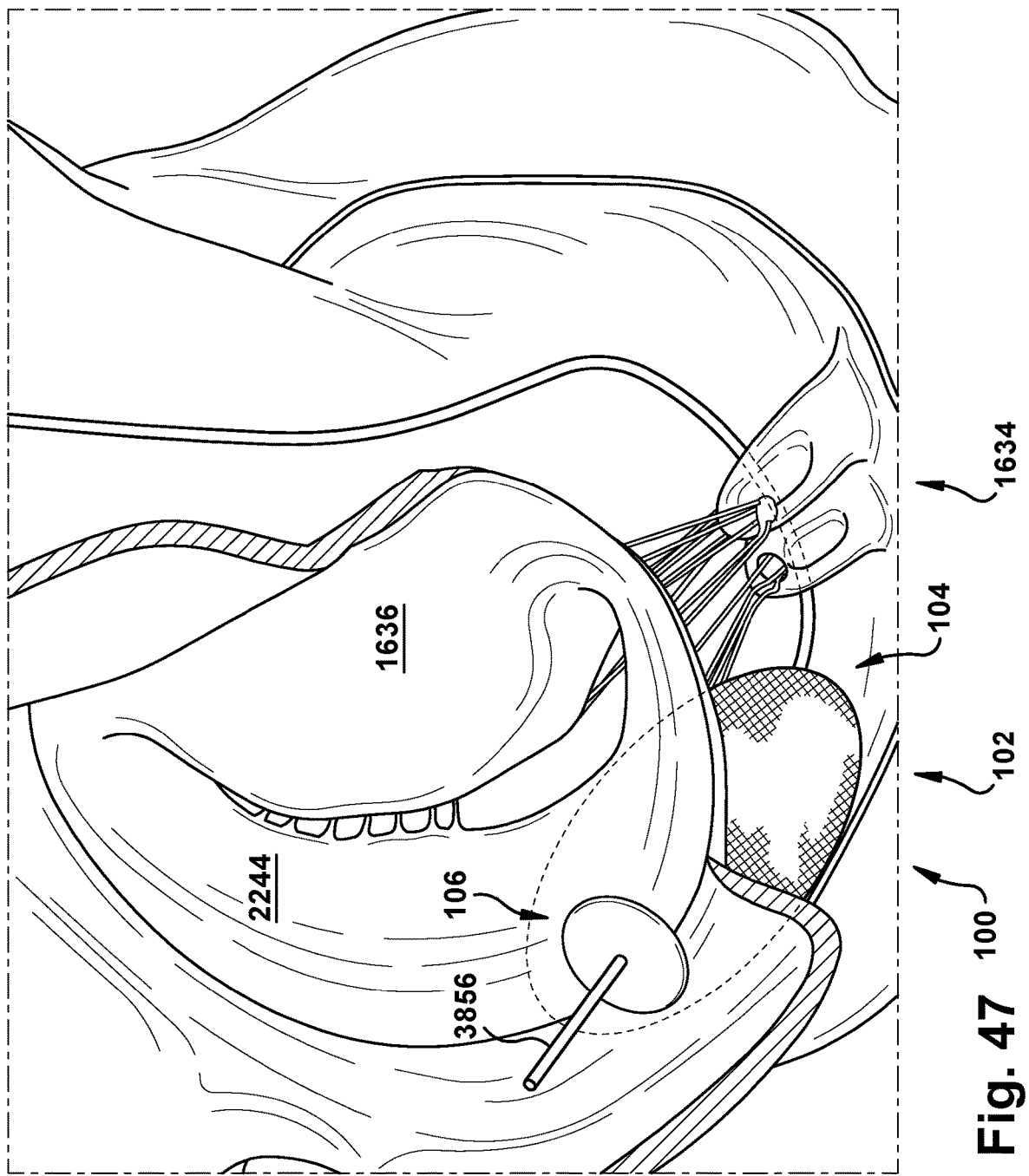

The subvalvular device 102 is maintained with the connector neck 108 penetrating longitudinally through at least one of a base of a posterior leaflet 2244 and an annulus of the mitral valve 1636 at the manufactured puncture site 4060. Then, as shown in FIGS. 45-48, the subvalvular supporting portion 104 is deployed longitudinally adjacent the manufactured puncture site 4060 at a location on a lower side of the leaflet 2244, with at least a portion of the supporter perimeter wall 214 contacting a subvalvular cardiac wall 2242 adjacent to the valve 1636. At least one of a base of a posterior leaflet 2244 and an annulus of the mitral valve 1636 is interposed longitudinally between the anchor portion 106 and the subvalvular supporting portion 104 to locate the subvalvular device 102 in an operating position with respect to the valve 1636, as shown in FIGS. 46-48.

The deployment of the anchor portion 106 and/or the subvalvular supporting portion 104 can occur in any suitable manner, and will depend upon the nature of those components. For example, when the anchor portion 106 and/or the subvalvular supporting portion 104 includes a braided mesh strand construct, deployment may include expanding the braided mesh strand construct comprising at least a portion of the anchor portion 106 and/or the subvalvular supporting portion 104. In other situations, deployment of the anchor portion 106 and/or the subvalvular supporting portion 104 may include inflating a balloon comprising at least a portion of the anchor portion 106 and/or the subvalvular supporting portion 104; or bowing radially outward from each other a body portion of each strut of a plurality of longitudinally oriented struts comprising at least a portion of the anchor portion 106 and/or the subvalvular supporting portion 104.

Regardless of the exact nature in which the anchor portion 106 and/or the subvalvular supporting portion 104 are deployed, though, once the subvalvular device 102 is in place in the operating position, movement of the leaflet 2244 is resisted during heart operation to substantially support the leaflet. During the surgical procedure, it is contemplated that mechanical function of the valve 1636 could be tested with the subvalvular device 102 maintained in the operating position. At least one of a position of the subvalvular device 102 and at least one dimension of the subvalvular device 102 could be adjusted, such as by deploying the subvalvular device, or components thereof, more fully responsive to results of the mechanical function testing. As a result, the user can "fine tune" the apparatus 100 to achieve desired results upon the regurgitation characteristics of the valve 1636.

Viewing the sequence from FIGS. 47-48, the guidewire 3856 may be removed from the heart 1634 of the patient at any desired time during the surgical procedure, though it is contemplated that the guidewire 3856 will be removed (optionally including releasing at least a portion of the apparatus 100 therefrom) at the final conclusion of the surgical procedure, in most cases. The surgical incision can then be closed and the surgical procedure concluded in a known manner. While the method shown in FIGS. 38-48 included the provision and deployment of a single subvalvular device 102 comprising the apparatus 100, it is contemplated that multiple subvalvular devices 102 could be installed similarly during the same surgical procedure, in which case the guidewire 3856 will likely remain in the heart 1634 until all of the subvalvular devices 102 have been deployed to the user's satisfaction.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:

1. A method for at least partially supporting a leaflet of a regurgitant heart valve, the method comprising:
   placing a guidewire into a heart of a patient;
   advancing the guidewire longitudinally through at least one of a base of the leaflet and an annulus of the heart valve;
   penetrating completely through at least one of the base of the leaflet and the annulus of the heart valve to create a manufactured puncture site;
   providing a subvalvular device including
      a subvalvular supporting portion including a leaflet-contacting upper supporter surface longitudinally spaced from an oppositely facing lower supporter surface, a supporter perimeter wall extending longitudinally between, and integrally and contiguously formed with both of, the upper and lower supporter surfaces,
      an anchor portion adjacent to, and longitudinally spaced from, the upper supporter surface, the anchor portion including a leaflet-contacting lower anchor surface longitudinally spaced from an oppositely facing upper anchor surface, an anchor perimeter wall extending longitudinally between, and integrally and contiguously formed with both of, the upper and lower anchor surfaces, and
      a connector neck interposed longitudinally between, and directly attached to both of, the upper supporter surface and the lower anchor surface;
   advancing the subvalvular device into the heart;
   advancing the anchor portion through the manufactured puncture site to a predetermined anchor location on an upper side of the leaflet;
   deploying the anchor portion at the predetermined anchor location;
   maintaining the subvalvular device with the connector neck penetrating longitudinally through at least one of the base of the leaflet and the annulus of the heart valve at the manufactured puncture site;
   deploying the subvalvular supporting portion longitudinally adjacent the manufactured puncture site at a location on a lower side of the leaflet, with at least a portion of the supporter perimeter wall contacting a subvalvular cardiac wall adjacent to the valve;
   interposing at least one of the base of the leaflet and the annulus of the heart valve longitudinally between the anchor portion and the subvalvular supporting portion to locate the subvalvular device in an operating position with respect to the valve; and
   with the subvalvular device, resisting movement of the leaflet during heart operation to substantially support the leaflet.

2. The method of claim 1, including:
   placing a variable-dimension sizer adjacent the manufactured puncture site at a location on a lower side of the leaflet; and
   varying at least one dimension of the sizer to ascertain the presence of a predetermined effect upon the leaflet responsive to the at least one sizer dimension.

3. The method of claim 2, including:
   removing the sizer from the patient; and
   selecting at least one dimension of the subvalvular device responsive to the at least one sizer dimension.

4. The method of claim 1, wherein at least one of the subvalvular supporting portion and the anchor portion is substantially formed of braided mesh strands.

5. The method of claim 4, wherein both of the subvalvular supporting portion and the anchor portion are substantially formed of braided mesh strands.

6. The method of claim 1, wherein one of the subvalvular supporting portion and the anchor portion is substantially formed of braided mesh strands and the other of the subvalvular supporting portion and the anchor portion is a balloon.

7. The method of claim 1, wherein the subvalvular supporting portion, anchor portion, and connector neck collectively enclose a single contiguous interior volume.

8. The method of claim 1, wherein both of the upper and lower supporter surfaces are substantially planar and mutually parallel.

9. The method of claim 1, wherein the anchor portion is a first anchor portion, and including deploying a second anchor portion at a second predetermined anchor location.

10. The method of claim 1, wherein the subvalvular supporting portion and the anchor portion are both circularly symmetrical about the connector neck.

11. The method of claim 1, including attaching a separately provided covering material to a majority of an outer surface of the subvalvular device.

12. A method of modifying a heart valve of a patient, the method comprising:
   placing a guidewire into a heart of a patient;
   advancing the guidewire completely through at least one of the leaflet and the annulus of the heart valve to create a manufactured puncture site;
   providing a subvalvular device including
      a leaflet-contacting supporting portion to sit below the heart valve,
      an anchor portion to sit above the heart valve, and
      a connector neck interposed longitudinally between, and directly attached to both of, the leaflet-contacting supporting portion, and the anchor portion,
      at least one of the supporting portion and the anchor portion being substantially torus-shaped;
   advancing the subvalvular device into the heart;
   deploying the subvalvular device with the connector neck penetrating longitudinally through at least one of the base of the leaflet and the annulus of the heart valve at the manufactured puncture site, so the leaflet-contacting supporting portion sits longitudinally adjacent the manufactured puncture site at a location on a lower side of the leaflet; and with the subvalvular device, substantially manipulating the leaflet to reduce regurgitation in the heart valve.

13. The method of claim 12, including:

placing a variable-dimension sizer adjacent the manufactured puncture site at a location on a lower side of the leaflet; and varying at least one dimension of the sizer to ascertain the presence of a predetermined effect upon the leaflet responsive to the at least one sizer dimension.

14. The method of claim 12, including:

removing the sizer from the patient; and selecting at least one dimension of the subvalvular device responsive to the at least one sizer dimension.

15. The method of claim 12, wherein at least one of the subvalvular supporting portion and the anchor portion is substantially formed of braided mesh strands.

16. The method of claim 15, wherein both of the subvalvular supporting portion and the anchor portion are substantially formed of braided mesh strands.

17. The method of claim 12, wherein one of the subvalvular supporting portion and the anchor portion is substantially formed of braided mesh strands and the other of the subvalvular supporting portion and the anchor portion is a balloon.

18. The method of claim 12, wherein the subvalvular supporting portion, anchor portion, and connector neck collectively enclose a single contiguous interior volume.

19. The method of claim 12, wherein the anchor portion is a first anchor portion, and including deploying a second anchor portion at a second predetermined anchor location.

20. The method of claim 12, including attaching a separately provided covering material to a majority of an outer surface of the subvalvular device.

21. A method of modifying a heart valve of a patient, the method comprising:

placing a guidewire into a heart of a patient;

advancing the guidewire completely through at least one of the leaflet and the annulus of the heart valve to create a manufactured puncture site;

providing a subvalvular device including a leaflet-contacting supporting portion to sit below the heart valve, an anchor portion to sit above the heart valve, the anchor portion being adjacent to, and longitudinally spaced from, the leaflet-contacting supporting portion, the anchor portion including a leaflet-contacting lower anchor surface longitudinally spaced from an oppositely facing upper anchor surface, and an anchor perimeter wall extending longitudinally between, and integrally and contiguously formed with both of, the upper and lower anchor surfaces, and a connector neck interposed longitudinally between, and directly attached to both of, the leaflet-contacting supporting portion, and the anchor portion;

advancing the subvalvular device into the heart;

deploying the subvalvular device with the connector neck penetrating longitudinally through at least one of the base of the leaflet and the annulus of the heart valve at the manufactured puncture site, so the leaflet-contacting supporting portion sits longitudinally adjacent the manufactured puncture site at a location on a lower side of the leaflet; and with the subvalvular device, substantially manipulating the leaflet to reduce regurgitation in the heart valve.

22. The method of claim 21, including:

placing a variable-dimension sizer adjacent the manufactured puncture site at a location on a lower side of the leaflet; and varying at least one dimension of the sizer to ascertain the presence of a predetermined effect upon the leaflet responsive to the at least one sizer dimension.

23. The method of claim 21, including:

removing the sizer from the patient; and selecting at least one dimension of the subvalvular device responsive to the at least one sizer dimension.

24. The method of claim 21, wherein the subvalvular supporting portion, anchor portion, and connector neck collectively enclose a single contiguous interior volume.

25. The method of claim 21, wherein the anchor portion is a first anchor portion, and including deploying a second anchor portion at a second predetermined anchor location.

* * * * *